(12) United States Patent
Tegreene et al.

(10) Patent No.: US 9,378,366 B2
(45) Date of Patent: Jun. 28, 2016

(54) DECEPTIVE INDICIA NOTIFICATION IN A COMMUNICATIONS INTERACTION

(75) Inventors: Clarence T. Tegreene, Mercer Island, WA (US); Royce A. Levien, Lexington, MA (US); Richard T. Lord, Tacoma, WA (US); Robert W. Lord, Seattle, WA (US); Mark A. Malamud, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/373,798

(22) Filed: Nov. 30, 2011

(65) Prior Publication Data

US 2013/0139253 A1 May 30, 2013

Related U.S. Application Data

(63) Continuation-in-part of application No. 13/373,799, filed on Nov. 30, 2011.

(51) Int. Cl.
| | | |
|---|---|---|
| *G06F 21/55* | (2013.01) | |
| *H04N 21/422* | (2011.01) | |
| *H04N 21/439* | (2011.01) | |
| *H04N 21/44* | (2011.01) | |
| *H04N 21/442* | (2011.01) | |
| *H04N 21/4788* | (2011.01) | |
| *H04N 21/84* | (2011.01) | |

(Continued)

(52) U.S. Cl.
CPC ............. *G06F 21/554* (2013.01); *A61B 5/16* (2013.01); *H04N 21/42201* (2013.01); *H04N 21/4394* (2013.01); *H04N 21/44008* (2013.01); *H04N 21/44218* (2013.01); *H04N 21/4788* (2013.01); *H04N 21/84* (2013.01); *A61B 5/021* (2013.01); *A61B 5/024* (2013.01)

(58) Field of Classification Search
None
See application file for complete search history.

(56) References Cited

U.S. PATENT DOCUMENTS 5,771,261 A     6/1998  Anbar
5,853,005 A  *  12/1998  Scanlon ..................... 600/459

(Continued)

FOREIGN PATENT DOCUMENTS

EP          1872719 A1      2/2008

OTHER PUBLICATIONS

"Continuous Noninvasive Blood Pressure Measurement by Near Infra Red CCD Camera and Pulse Transmit Time System"—Zurek, P. Krejcar, O. Penhaker, M. Cerny, M. Frischer, R., 2010 Second International Conference on Computer Engineering and Applications (ICCEA); Issue Date: Mar. 19-21, 2010; vol. 2, pp. 449-453.

(Continued)

*Primary Examiner* — David Le
(74) *Attorney, Agent, or Firm* — Suiter Swantz pc llo

(57) ABSTRACT

Systems, methods, computer-readable storage mediums including computer-readable instructions and/or circuitry for monitoring deceptive indicia in communications content may implement operations including, but not limited to: receiving one or more signals associated with communication content provided by a first participant in a communications interaction; detecting one or more indicia of deception associated with the one or more signals associated with the communication content; and providing a notification associated with the one or more indicia of deception associated with the communication content to a second participant in the communications interaction receiving the communication content.

26 Claims, 16 Drawing Sheets

(51) Int. Cl.
*A61B 5/16* (2006.01)
*A61B 5/021* (2006.01)
*A61B 5/024* (2006.01)

(56) References Cited

U.S. PATENT DOCUMENTS

| | | |
|---|---|---|
| 6,837,615 B2 | 1/2005 | Newman |
| 6,959,322 B2 | 10/2005 | Ludwig et al. |
| 6,996,256 B2 | 2/2006 | Pavlidis |
| 7,027,621 B1 | 4/2006 | Prokoski |
| 7,111,980 B2 | 9/2006 | Pavlidis et al. |
| 7,138,905 B2 | 11/2006 | Pavlidis et al. |
| 7,321,855 B2 | 1/2008 | Humble |
| 7,388,971 B2 | 6/2008 | Rice et al. |
| 7,437,766 B2 | 10/2008 | Cohen et al. |
| 7,849,502 B1 | 12/2010 | Bloch et al. |
| 7,853,445 B2 | 12/2010 | Bachenko et al. |
| 8,145,562 B2 | 3/2012 | Wasserblat et al. |
| 8,224,907 B2 | 7/2012 | Cohen et al. |
| 8,347,399 B2 | 1/2013 | Levien et al. |
| 8,543,196 B2 | 9/2013 | Ning |
| 8,577,446 B2 | 11/2013 | Kyle et al. |
| 2002/0066034 A1* | 5/2002 | Schlossberg et al. ......... 713/201 |
| 2002/0078357 A1 | 6/2002 | Bruekers et al. |
| 2003/0012253 A1 | 1/2003 | Pavlidis |
| 2003/0149344 A1 | 8/2003 | Nizan |
| 2003/0236995 A1* | 12/2003 | Fretwell, Jr. .................. 713/200 |
| 2004/0143170 A1 | 7/2004 | DuRousseau |
| 2004/0181145 A1 | 9/2004 | Al Bandar et al. |
| 2005/0097320 A1 | 5/2005 | Golan et al. |
| 2005/0143629 A1 | 6/2005 | Farwell |
| 2005/0144256 A1 | 6/2005 | Blumberg |
| 2005/0185779 A1 | 8/2005 | Toms |
| 2005/0232471 A1 | 10/2005 | Baer |
| 2005/0240956 A1 | 10/2005 | Smith et al. |
| 2005/0288954 A1 | 12/2005 | McCarthy et al. |
| 2006/0123482 A1* | 6/2006 | Aaron .............................. 726/25 |
| 2007/0038778 A1 | 2/2007 | Miao et al. |
| 2007/0177017 A1 | 8/2007 | Kyle et al. |
| 2007/0192108 A1 | 8/2007 | Konchitsky |
| 2007/0214504 A1* | 9/2007 | Milani Comparetti et al. . 726/23 |
| 2007/0270659 A1 | 11/2007 | Giegerich |
| 2008/0059198 A1 | 3/2008 | Maislos et al. |
| 2008/0208016 A1* | 8/2008 | Hughes et al. ................. 600/301 |
| 2008/0260212 A1* | 10/2008 | Moskal et al. ................. 382/118 |
| 2008/0282324 A1 | 11/2008 | Hoal |
| 2009/0023422 A1 | 1/2009 | MacInnis et al. |
| 2009/0023428 A1 | 1/2009 | Behzad et al. |
| 2009/0177979 A1* | 7/2009 | Garbow et al. ............... 715/757 |
| 2009/0193293 A1* | 7/2009 | Stolfo et al. .................... 714/26 |
| 2009/0254988 A1* | 10/2009 | Nonaka et al. ................. 726/22 |
| 2009/0254998 A1 | 10/2009 | Wilson |
| 2009/0299154 A1 | 12/2009 | Segman |
| 2010/0039218 A1 | 2/2010 | Cohen et al. |
| 2010/0042667 A1 | 2/2010 | Cohen et al. |
| 2010/0042669 A1 | 2/2010 | Cohen et al. |
| 2010/0067798 A1 | 3/2010 | Hung et al. |
| 2010/0099975 A1 | 4/2010 | Faro et al. |
| 2010/0132038 A1* | 5/2010 | Zaitsev ........................... 726/22 |
| 2010/0191077 A1 | 7/2010 | O'Kane |
| 2010/0246835 A1 | 9/2010 | Dooling et al. |
| 2010/0318595 A1 | 12/2010 | Cohen et al. |
| 2011/0004939 A1 | 1/2011 | Cohen et al. |
| 2011/0004940 A1 | 1/2011 | Cohen et al. |
| 2011/0035472 A1* | 2/2011 | Tucker et al. .................. 709/221 |
| 2011/0041061 A1 | 2/2011 | Cohen et al. |
| 2011/0041185 A1 | 2/2011 | Cohen et al. |
| 2011/0043759 A1 | 2/2011 | Bushinsky |
| 2011/0081018 A1 | 4/2011 | Cohen et al. |
| 2011/0083010 A1 | 4/2011 | Cohen et al. |
| 2011/0093806 A1 | 4/2011 | Cohen et al. |
| 2011/0107427 A1 | 5/2011 | Cohen et al. |
| 2011/0110518 A1 | 5/2011 | Cohen et al. |
| 2011/0131409 A1 | 6/2011 | Cohen et al. |
| 2011/0154020 A1 | 6/2011 | Cohen et al. |
| 2011/0161217 A1 | 6/2011 | Cohen et al. |
| 2011/0166972 A1 | 7/2011 | Cohen et al. |
| 2011/0166973 A1 | 7/2011 | Cohen et al. |
| 2011/0166974 A1 | 7/2011 | Cohen et al. |
| 2011/0169603 A1 | 7/2011 | Fithian et al. |
| 2011/0173440 A1 | 7/2011 | Cohen et al. |
| 2011/0176667 A1 | 7/2011 | Kumar |
| 2011/0181684 A1 | 7/2011 | Salamatov et al. |
| 2011/0224979 A1 | 9/2011 | Raux |
| 2011/0295392 A1 | 12/2011 | Cunnington et al. |
| 2012/0150762 A1 | 6/2012 | Ormerod |
| 2012/0254333 A1 | 10/2012 | Chandramouli et al. |
| 2013/0046531 A1 | 2/2013 | Chandramouli et al. |
| 2013/0138428 A1 | 5/2013 | Chandramouli et al. |
| 2014/0278629 A1 | 9/2014 | Stephenson et al. |
| 2014/0355861 A1 | 12/2014 | Nirenberg et al. |
| 2015/0095162 A1 | 4/2015 | Jakobson et al. |

OTHER PUBLICATIONS

"A novel method to detect Heart Beat Rate using a mobile phone"—2010 Annual International Conference of the IEEE Engineering in Medicine and Biology Society (EMBC); Pelegris, Banitsas, Orbach and Marias; Aug. 31 2010-Sep. 4 2010; pp. 5488-5491.

"Towards Macro- and Micro-Expression Spotting in Video Using Strain Patterns"—Shreve, Godavarthy, Manohar, Goldgof, Sarkar; Dec. 7-8, 2009; pp. 1-6; http://figment.csee.usf.edu/~vmanohar/WACV09_Expression_Spotting.pdf; Printed Feb. 28, 2012.

* cited by examiner

DECEPTIVE INDICIA NOTIFICATION IN A COMMUNICATIONS INTERACTION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of the U.S. patent application Ser. No. 13/373,799, entitled DECPTIVE INDCA NOTIFICATION IN A COMMUNICATIONS INTERACTION, naming Clarence T. Tegreene, as inventor, filed Nov. 30, 2011, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

Systems, methods, computer-readable storage mediums including computer-readable instructions and/or circuitry for monitoring deceptive indicia in communications content may implement operations including, but not limited to: receiving one or more signals associated with communication content provided by a first participant in a communications interaction; detecting one or more indicia of deception associated with the one or more signals associated with the communication content; and providing a notification associated with the one or more indicia of deception associated with the communication content to a second participant in the communications interaction receiving the communication content.

In one or more various aspects, related systems include but are not limited to circuitry and/or programming for effecting the herein referenced aspects; the circuitry and/or programming can be virtually any combination of hardware, software, and/or firmware configured to effect the herein-referenced method aspects depending upon the design choices of the system designer.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
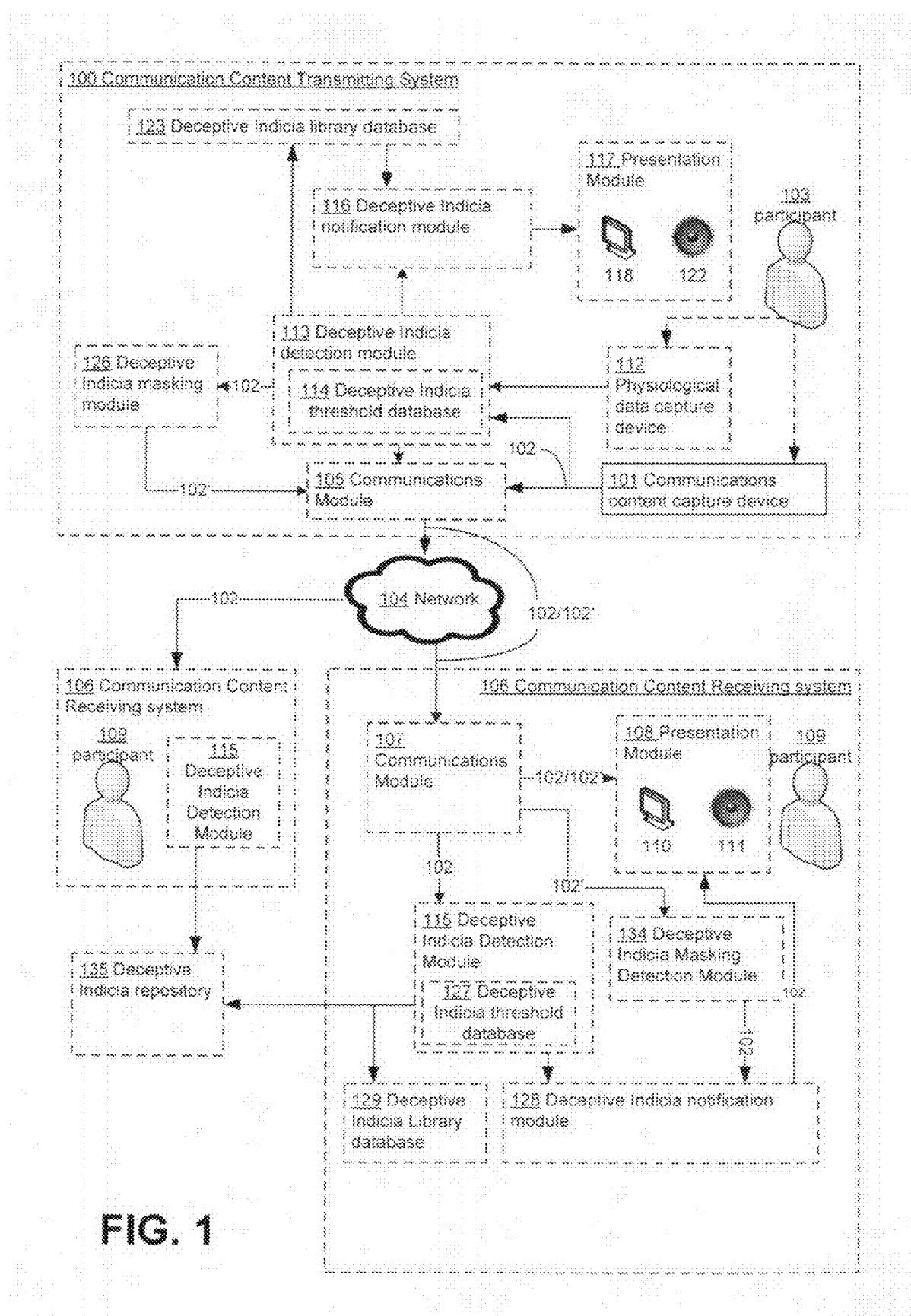
FIG. 1 shows a high-level block diagram of an operational environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Remote communication systems are ubiquitous in today's society. Individuals who are remote from one another may communicate using a plethora of communications systems such as land line telephones, mobile communication devices (e.g. mobile phones, tablet computers, etc.), networked video conferencing (e.g. Cisco TelePresence), and the like. During such communications interactions (e.g. phone calls, video conferences, etc.), participants may transmit and receive communications content (e.g. voice/audio data, video data, etc.) to various other remote participants.

For example, as shown in FIG. 1, a communications content transmitting system 100 may include a communications content capture device 101. The communications content capture device 101 may include, but is not limited to, a video capture device (e.g. a digital camera, web cam, teleconferencing camera, etc.), an audio capture device (e.g. a microphone, telephone), and the like. The communications content 102 captured from a content-generating participant 103 by the communications content capture device 101 may be transmitted to a communications network 104 via a communications module 105 of the communications content transmitting system 100. The communications module 105 may include a network adapter configured to translate the communications content 102 captured by the communications content capture device 101 according to a defined network protocol for the network 104 so as to enable transmission of the communications content 102 over the network 104. For example, the communications module 105 may include a wired network adapter (e.g. an Ethernet adapter), a cellular network adapter, a Wi-Fi network adapter, and the like.

As further shown in FIG. 1, the communications content 102 may be transmitted across the network 104 to a communication content receiving system 106. The communication content receiving system 106 may include a communications module 107 similar to the communications module 105 of the communications content transmitting system 100. For example, the communications module 107 may include a wired network adapter (e.g. an Ethernet adapter), a cellular network adapter, a Wi-Fi network adapter, and the like. The communications module 107 may translate communications content 102 transmitted across the network 104 according to the network protocol back into its native audio and/or video format. The communications content 102 may then be provided to a presentation module 108 where the communications content 102 may be displayed to a content-receiving participant 109 via a display device 110 in the case of video communications content 102 or broadcast to the content-receiving participant 109 via an audio speaker 111 in the case of audio communications content 102 so as to enable the content-receiving participant 109 to view and/or hear the communications content 102 generated by the content-generating participant 103.

It may be the case that such communications content 102 may be provided in the context of communications between the content-generating participant 103 and the content-receiving participant 109 where the content-generating participant 103 may have a motivation to provide deceptive information to the content-receiving participant 109. For example, the content-generating participant 103 and the content-receiving participant 109 may be communicating regarding a mutual business transaction where a negotiation of terms is occurring. As such, it may be the case that the content-generating participant 103 may attempt to present deceptive information (e.g. information which, according to one or more objective standards, is untrue) in an attempt to obtains terms of the business transaction that are more favorable for the side of the content-generating participant 103. As a specific example, the content-generating participant 103 may provide communications content 102 indicating that a maximum purchase price for a transaction is actually less that an authorized purchase price.

In such scenarios where the content-generating participant 103 may have a motivation to provide deceptive communications content 102 or, conversely, where the content-receiving participant 109 may believe that the content-generating participant 103 has such a motivation, various physiological indicia may be monitored to determine the likelihood that such deception is, in fact occurring.

For example, as shown in FIG. 1, the communications content transmitting system 100 may include a physiological data capture device 112. The physiological data capture device 112 may be a device configured to capture data associated with one or more physical conditions of the content-generating participant 103 such as heart rate, blood pressure, breathing patterns, perspiration levels, and the like. The physiological data capture device 112 may include, but is not limited to, a heart rate monitor (e.g. an EKG), a pressure transducer (e.g. a blood pressure monitoring cuff), a thermometer, a skin conductivity sensor, an IR sensor, a high-resolution camera, a microphone, and the like. Physiological data obtained by the physiological data capture device 112 may be provided to a which may analyze the physiological data (e.g. compare the data to one or more threshold levels) to determine if the physiological data represents and indicia of deception.

Additionally, the communications content 102, itself, received via the communications content capture device 101 may be provided to the deceptive indicia detection module 113 for analysis of the communications content 102 to determine if the communications content 102 represents and indicia of deception. For example, the audio and/or video of the communications content 102 may be analyzed to determine the various physiological characteristics such as heart rate, blood pressure, breathing patterns, perspiration levels as well as other parameters such as eye dilation, eye movements, voice stress, language constructs, and the like.

Upon receipt of either physiological data from a physiological data capture device 112 or the communications content 102 received from the communications content capture device 101, such data may be analyzed for correspondence with one or more defined deceptive indicia threshold values maintained in a deceptive indicia threshold database 114. Exceeding one or more deceptive indicia threshold values may be an indicator that the content-generating participant 103 is presenting one or more physiological indicators, speech patterns and/or physical movements that may be interpreted by a content-receiving participant 109 as being associated with deception in the communications content 102.

In an exemplary embodiment, the physiological data capture device 112 may include a near infra red charge-coupled device camera. The near IR CCD camera may image one or more blood vessels of the content-generating participant 103. The deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate. The computed heart rate may be compared to a deceptive indicia threshold value maintained in the deceptive indicia threshold database 114. As an elevated heart rate may be an indicator of stress associated with providing deceptive communications content 102, a computed heart rate in excess of the deceptive indicia threshold value may be detected as indicia of deception in the communications content 102.

In another exemplary embodiment, the physiological data capture device 112 may include a near infra red charge-coupled device camera. The near IR CCD camera may image one or more blood vessels of the content-generating participant 103. The deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102.

In another exemplary embodiment, the communications content capture device 101 and/or the physiological data capture device 112 may include a high-resolution camera. The high-resolution camera may image the skin surface of the content-generating participant 103. The deceptive indicia detection module 113 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

In another exemplary embodiment, the communications content capture device 101 and/or the physiological data capture device 112 may include a high-resolution camera. The high-resolution camera may image the facial region of the content-generating participant 103. The deceptive indicia detection module 113 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception.

Further, certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

In another exemplary embodiment, the communications content capture device 101 and/or the physiological data capture device 112 may include a microphone. The microphone may capture an audio signal (e.g. speech content, a voice print, breathing, ambient noise, etc.) of the content-generating participant 103. The deceptive indicia detection module 113 may then analyze the audio signal and detect one or more characteristics of the audio signal.

For example, the deceptive indicia detection module 113 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 113 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102.

In a further example, the deceptive indicia detection module 113 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 113 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102.

In a case where a content-generating participant 103 is presenting one or more indicia of deception (e.g. physiological indicators, speech patterns and/or physical movements) that may be interpreted/detected by a content-receiving participant 109 (e.g. detected by deceptive indicia detection module 115 associated with the communication content receiving system 106) as being associated with deception, it may be desirable for the content-generating participant 103 be made aware of such indicia of deception so that the content-generating participant 103 may take remedial steps to mitigate such indicia in a case where the content-generating participant 103 desires to avoid presenting an indication of deception in the communications content 102, or alternately, introduce indicia of deception into communications content 102 where the content-generating participant 103 desires to present a false indication of deception in the communications content 102.

As such, the communications content transmitting system 100 may include a deceptive indicia notification module 116. The deceptive indicia notification module 116 may receive one or more signals from the deceptive indicia detection module 113 indicating the presence or absence of deceptive indicia in communications content 102 being provided to the content-receiving participant 109. Upon the receipt of one or more signals associated with the presence of indicia of deception in communications content 102 from the deceptive indicia detection module 113, the deceptive indicia notification module 116 may, in turn provide one or more signals to a presentation module 117 so that an indicator associated with the indicia of deception is presented to the content-generating participant 103.

Figure 2A:
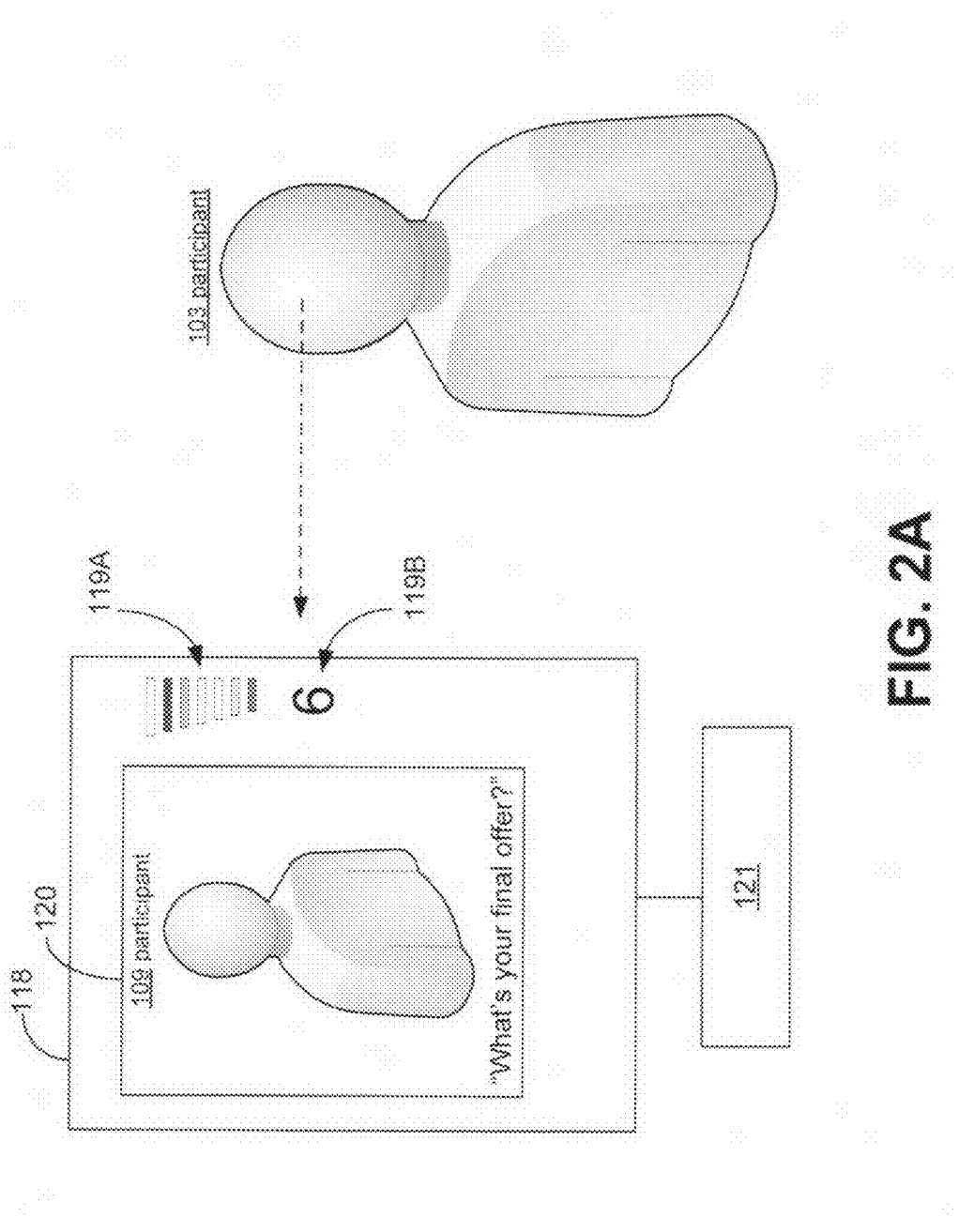
FIG. 2A shows an exemplary high-level block diagram of an exemplary system.

For example, upon the receipt of one or more signals associated with the presence of indicia of deception in communications content 102 from the deceptive indicia detection module 113, the deceptive indicia notification module 116 may provide one or more video signals to a deceptive indicia display device 118 (e.g. an LCD display) so that a visual indicator 119 associated with the indicia of deception is presented within a field of view of the content-generating participant 103. As shown in FIG. 2A, the deceptive indicia display device 118 may display a video conferencing interface 120 configured to present audio/video content from the content-receiving participant 109 during a communication interaction (e.g. at least one of audio and visual communication between at least the content-generating participant 103 and content-receiving participant 109). The deceptive indicia display device 118 may display a visual indicator 119A that presents a rate of occurrences of indicia of deception in the communications content 102, a visual indicator 119B that presents a cumulative number of occurrences of indicia of deception in the communications content 102, a color coded visual indicator 119A (e.g. "green" level indicating a low rate of occurrences of indicia of deception, a "yellow" level indicating a moderate rate of occurrences of indicia of deception, to a "red" level indicating a high rate of occurrences of indicia of deception). The visual indicator 119 may be a dynamic indicator that changes (e.g. moves from an indicated "high" rate of indicia of deception to an indicated "low" rate of indicia of deception) in real-time according to the type and/or amount of indicia of deception detected within communications content 102. The visual indicator 119 may provide an indication of the level of indicia of deception on a aggregate basis (e.g. occurrence metrics for multiple indicia of deception types, such as eye movement, formal language, etc. are combined into a single indicator for an "overall" view of the indicia of deception) or on an indicia-by-indicia basis (e.g. each indicia type is represented by a separate visual indicator 119).

Further, it will be noted that certain eye movements may be indicia of deception. For example, in the case of a right-handed person, movement of the eyes to the up and left may be indicative of a "constructed" response which may be indicative of deception. Conversely, movement of the eyes up and to the right may be indicative of a "memory recall" response which may be indicative of truthfulness. The above referenced conventions may be reversed for a left-handed person.

As such, the communications content transmitting system 100 may further include a user input device 121 (e.g. a keyboard, mouse, touch pad, touch screen, etc.) that may receive a user input from the content-generating participant 103 defining a "handedness" of the content-generating participant 103. The visual indicator 119 may be displayed on the deceptive indicia display device 118 according to the "handedness" of the content-generating participant 103 so that the act of looking at the visual indicator 119 by the content-generating participant 103 during a communications interaction is not, itself, an indicia of deception. Specifically, for a right-handed content-generating participant 103, the visual indicator 119 may be displayed on the right-hand side of the deceptive indicia display device 118. For a left-handed content-generating participant 103, the visual indicator 119 may be displayed on the left-hand side of the deceptive indicia display device 118 (not shown).

In another embodiment, the upon the receipt of one or more signals associated with the presence of indicia of deception in communications content 102 from the deceptive indicia detection module 113, the deceptive indicia notification module 116 may provide one or more audio signals to a deceptive indicia broadcast device 122 (e.g. an audio speaker, headset, earpiece, etc.) that an audio indicator (e.g. a notification sound effect such as a beep, a spoken message, etc.) associated with the indicia of deception is emitted to the content-generating participant 103.

In order to avoid presenting indicia of deception that rises to a level where it may be detectable by the content-receiving participant 109 via the deceptive indicia detection module 115 of communications module 107, the deceptive indicia detection module 113 may maintain two or more threshold values associated with a given indicia of deception in deceptive indicia threshold database 114 so as to provide a notification that a detectable incidence of deception has likely already occurred as well as to provide a predictive notification that an indicia of deception may occur in the future. For example, the first threshold value may be a predictive threshold value indicating that a number or rate of indicia of deception has occurred which rise to a level which is not likely to be a detectable incidence of deception but may be trending towards such a level. The second threshold value may be a detectable threshold value indicating that sufficient number of indicia of deception have been present in communications content 102 that a content-receiving participant 109 may detect it as an incidence of deception.

It may be the case that the deceptive indicia detection module 113 and deceptive indicia notification module 116 may perform deceptive indicia detection and notification in a substantially real-time manner during a communication interaction (e.g. a video conference) between the content-generating participant 103 and the content-receiving participant 109 to allow the content-generating participant 103 to monitor the communications content 102 for indicia of deception. Further, upon completion of a communications interaction, it may be advisable for a content-generating participant 103 to review the communications content 102 and any detected indicia of deception for education and/or training purposes. As such, during a communication interaction, the deceptive indicia detection module 115 may record the communications content 102 and apply one or more tags to the recorded communications content 102 according to detected occurrences of indicia of deception.

For example, during a communication interaction, the deceptive indicia detection module 115 may detect an incidence of indicia of deception. The deceptive indicia detection module 115 may sample a portion of the communications content 102 containing the detected incidence of indicia of deception and store an audio/video file containing the sampled portion of the communications content 102 containing the detected incidence of indicia of deception to a deceptive indicia library database 123. The audio/video file containing the sampled portion of the communications content 102 containing the detected incidence of indicia of deception may be annotated with information regarding the indicia of deception (e.g. the type of indicia of deception, the degree of deception indicated, etc.) to facilitate review of the detected indicia of deception.

In another example, during a communication interaction, the deceptive indicia detection module 115 may detect an incidence of indicia of deception. The deceptive indicia detection module 115 may record the communications content 102 as an audio/video file and apply a graphical element (e.g. a "flag" icon 124) to the audio/video file at a time associated with the detection of an incidence of indicia of deception. The recorded audio/video file containing the graphical element communications content 102 associated with the detected incidence of indicia of deception may be stored to the deceptive indicia library database 123.

In another example, during a communication interaction, the deceptive indicia detection module 115 may detect an incidence of indicia of deception. The deceptive indicia detection module 115 may store a time stamp associated with the detected incidence of the indicia of deception to the deceptive indicia library database 123.

In another example, a content-generating participant 103 may be independently aware of an occurrence of an indicia of deception contained in the communications content 102 (e.g. the content-generating participant 103 knows they have lied about a maximum authorized purchase price during a negotiation). In such a case, the communications content transmitting system 100 may receive a user input via user input device 121 indicative of an occurrence of indicia of deception in the communications content 102. The deceptive indicia detection module 115 may correlate the occurrence of the user input to detected indicia of deception and apply a tag (e.g. an audio/video sample, an insertion of a graphical element, storing a time stamp, etc.) to the communications content 102 according to the user input.

As described above, it may be advisable for a content-generating participant 103 to review the communications content 102 and any detected indicia of deception for education and/or training purposes. As such, following tagging of the communications content 102 according to the detected indicia of deception, the portions of the communications content 102 associated with the tagged indicia of deception may be replayed to the content-generating participant 103. For example, as shown in FIG. 2A, one or more tagged portions of the communications content 102 may be retrieved from the deceptive indicia library database 123 and displayed/broadcasted by the presentation module 117 via a review interface 125. The review interface 125 may include video playback functionality configured to present the communications content 102 according to the tags. For example, the review interface 125 may allow for the content-generating participant 103 to skip to portions of the communications content 102 associated with the tags. For example, the review interface 125 may provide a "skip to next" user interface element whereby a user input associated with the "skip to next" user interface element causes the review interface 125 to display/broadcast the next instance of the communications content 102 having a tag associated with a detection of indicia of deception.

In addition to providing a notification to the content-generating participant 103 that the communications content 102 provided to the content-receiving participant 109 may include one or more indicia of deception, one or more remedial measures may be taken to modify the communications content 102 to reduce or remove or, alternately, add or enhance the indicia of deception from the communications content 102 prior to providing the communications content 102 to the content-receiving participant 109. For example, as shown in FIG. 1, following detection of indicia of deception in the communications content 102 by the deceptive indicia detection module 115, the communications content 102 may be provided to a deceptive indicia masking module 126. The deceptive indicia masking module 126 may modify the communications content 102 to reduce or remove the detected indicia of deception within the communications content 102 to produce modified communications content 102'. Alternately, the deceptive indicia masking module 126 may modify the communications content 102 to add or enhance indicia of deception within the communications content 102 to produce modified communications content 102'. This modified communications content 102' may be provided to the content-receiving participant 109 in place of communications content 102.

Further, it may be the case that the content-receiving participant 109 wishes to determine the presence of indicia of deception in the communications content 102 and receive notification thereof. As such, the communication content receiving system 106 may include a deceptive indicia detection module 115 maintaining a deceptive indicia threshold database 127, a deceptive indicia notification module 128, a presentation module 108 and a deceptive indicia library database 129 employing functionality similar to the deceptive indicia detection module 113, deceptive indicia notification module 116, presentation module 117 and deceptive indicia library database 123 described above to detect and notify the content-receiving participant 109 of the presence of indicia of deception in the communications content 102 as well as generate an indicia of deception profile for the content-generating participant 103 to be stored in deceptive indicia library database 129.

For example, as shown in FIG. 1, communications content 102 received by the communication content receiving system 106 from the communications content transmitting system 100 via the communications module 107 may be provided to the deceptive indicia detection module 115 for analysis of the communications content 102 to determine if the communications content 102 represents an indicia of deception. For example, the audio and/or video of the communications content 102 may be analyzed to determine the various physiological characteristics such as heart rate, blood pressure, breathing patterns, perspiration levels as well as other parameters such as eye dilation, eye movements, voice stress, language constructs, and the like of the content-generating participant 103.

Upon receipt of the communications content 102 from the communications content transmitting system 100, such data may be analyzed for correspondence with one or more defined deceptive indicia threshold values maintained in the deceptive indicia threshold database 127. Exceeding one or more deceptive indicia threshold values may be an indicator that the content-generating participant 103 is presenting one or more physiological indicators, speech patterns and/or physical movements that may be associated with deception in the communications content 102.

In an exemplary embodiment, the communications content capture device 101 may include a high-resolution camera (e.g. a camera having a resolution of at least 720 lines in a vertical direction). A high-resolution camera image may include sufficient resolution to image the movement of one or more blood vessels (e.g. the external carotid artery, external jugular vein, superficial temporal artery, etc.) of the content-generating participant 103. The deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate for the content-generating participant 103. The computed heart rate may be compared to a deceptive indicia threshold value maintained in the deceptive indicia threshold database 127. As an elevated heart rate may be an indicator of stress associated with providing deceptive communications content 102, a computed heart rate in excess of the deceptive indicia threshold value may be detected as indicia of deception in the communications content 102.

Alternately, deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102.

In another exemplary embodiment, the high-resolution camera may image the skin surface of the content-generating participant 103. The deceptive indicia detection module 115 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

In another exemplary embodiment, the high-resolution camera may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception.

Further, certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

In another exemplary embodiment, the communications content capture device 101 may include a microphone. The microphone may capture an audio signal (e.g. speech content, a voice print, breathing, ambient noise, etc.) of the content-generating participant 103. The deceptive indicia detection module 115 may then analyze the audio signal and detect one or more characteristics of the audio signal.

For example, the deceptive indicia detection module 115 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 115 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102.

In a further example, the deceptive indicia detection module 115 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 115 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102.

In a case where a content-generating participant 103 is presenting one or more indicia of deception (e.g. physiological indicators, speech patterns and/or physical movements) that may be interpreted/detected by a content-receiving participant 109 (e.g. detected by the deceptive indicia detection module 115 associated with the communication content receiving system 106) as being associated with deception, it may be desirable for the content-receiving participant 109 to be made aware of such indicia of deception so that the content-receiving participant 109 may account for such deception in considering the communications content 102.

As such, the communication content receiving system 106 may include a deceptive indicia notification module 128. The deceptive indicia notification module 128 may receive one or more signals from the deceptive indicia detection module 115 indicating the presence or absence of deceptive indicia in communications content 102 being provided to the content-receiving participant 109. Upon the receipt of one or more signals associated with the presence of indicia of deception in communications content 102 from the deceptive indicia detection module 115, the deceptive indicia notification module 128 may, in turn provide one or more signals to a presentation module 108 so that an indicator associated with the indicia of deception is presented to the content-receiving participants 109.

Figure 3A:
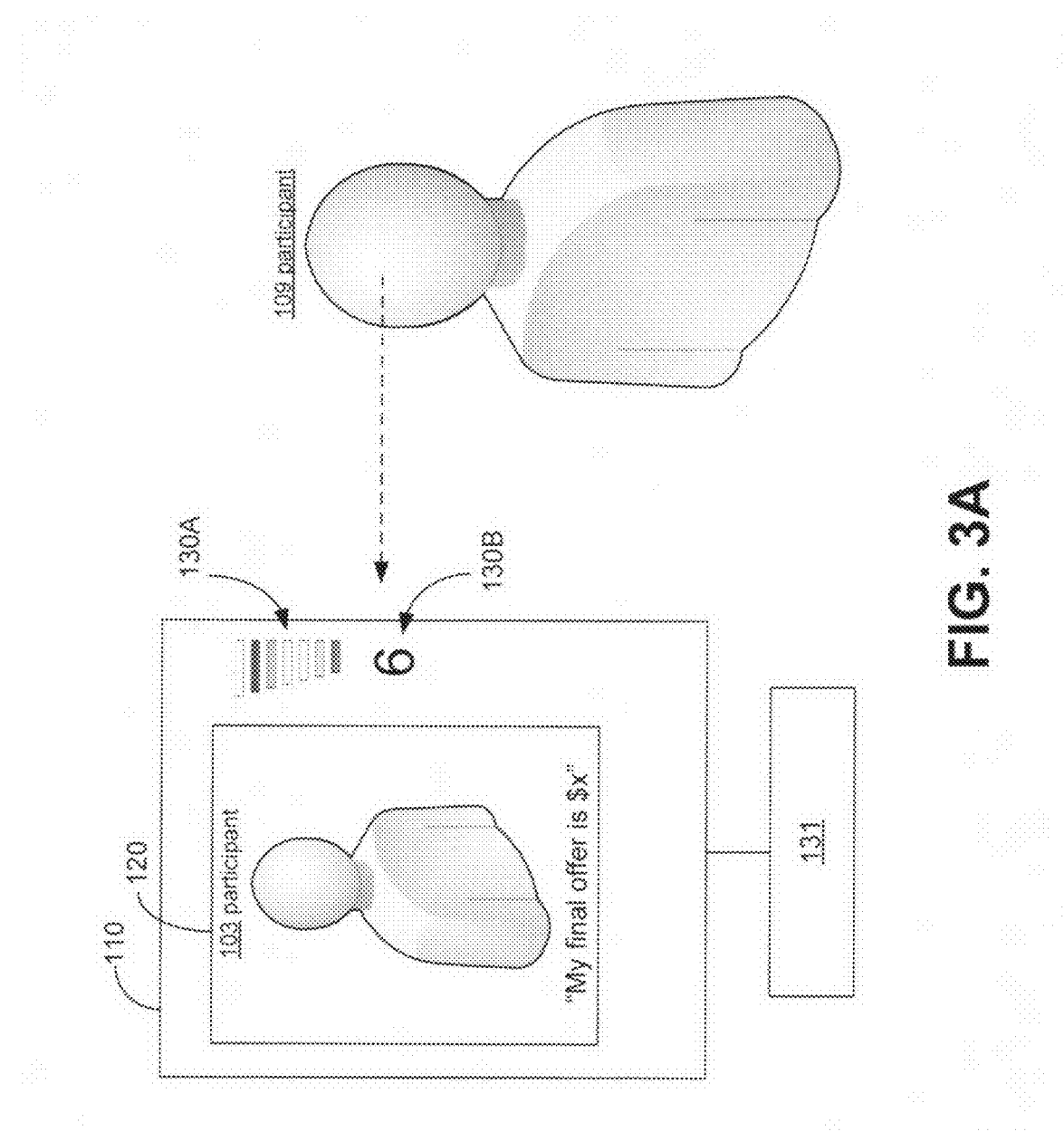
FIG. 3A shows an exemplary high-level block diagram of an exemplary system.

For example, upon the receipt of one or more signals associated with the presence of indicia of deception in communications content 102 from the deceptive indicia detection module 115, the deceptive indicia notification module 128 may provide one or more video signals to a display device 110 (e.g. an LCD display) so that a visual indicator 130 associated with the indicia of deception is presented within a field of view of the content-generating participant 103. As shown in FIG. 3A, the display device 110 may display a video conferencing interface 120 configured to present audio/video content to the content-receiving participant 109 during a communication interaction (e.g. at least one of audio and visual communication between at least the content-generating participant 103 and content-receiving participant 109). The display device 110 may display a visual indicator 130A that presents a rate of occurrences of indicia of deception in the communications content 102, a visual indicator 130B that presents a cumulative number of occurrences of indicia of deception in the communications content 102, a color coded visual indicator 130A (e.g. "green" level indicating a low rate of occurrences of indicia of deception, a "yellow" level indicating a moderate rate of occurrences of indicia of deception, to a "red" level indicating a high rate of occurrences of indicia of deception). The visual indicator 130 may be a dynamic indicator that changes (e.g. moves from an indicated "high" rate of indicia of deception to an indicated "low" rate of indicia of deception) in real-time according to the type and/or amount of indicia of deception detected within communications content 102. The visual indicator 130 may provide an indication of the level of indicia of deception on a aggregate basis (e.g. occurrence metrics for multiple indicia of deception types, such as eye movement, formal language, etc. are combined into a single indicator for an "overall" view of the indicia of deception) or on an indicia-by-indicia basis (e.g. each indicia type is represented by a separate visual indicator 130).

Further, it will be noted that certain eye movements may be indicia of deception. For example, in the case of a right-handed person, movement of the eyes to the up and left may be indicative of a "constructed" response which may be indicative of deception. Conversely, movement of the eyes up and to the right may be indicative of a "memory recall" response which may be indicative of truthfulness. The above referenced conventions may be reversed for a left-handed person.

As such, the communication content receiving system 106 may further include a user input device 131 (e.g. a keyboard, mouse, touch pad, touch screen, etc.) that may receive a user input from the content-receiving participant 109 defining a "handedness" of the content-receiving participant 109. The visual indicator 130 may be displayed on the display device 110 according to the "handedness" of the content-receiving participant 109 so that the act of looking at the visual indicator 130 by the content-receiving participant 109 during a communications interaction is not, itself, an indicia of deception by the content-receiving participant 109. Specifically, for a right-handed content-receiving participant 109, the visual indicator 130 may be displayed on the right-hand side of the display device 110. For a left-handed content-receiving participant 109, the visual indicator 130 may be displayed on the left-hand side of the display device 110 (not shown).

In another embodiment, the upon the receipt of one or more signals associated with the presence of indicia of deception in communications content 102 from the deceptive indicia detection module 115, the deceptive indicia notification module 128 may provide one or more audio signals to a audio speaker 111 (e.g. an audio speaker, headset, earpiece, etc.) that an audio indicator (e.g. a notification sound effect such as a beep, a spoken message, etc.) associated with the indicia of deception is emitted to the content-receiving participant 109.

In order to provide predictive detection of indicia of deception, the deceptive indicia detection module 115 may maintain two or more threshold values associated with a given indicia of deception in deceptive indicia threshold database 127 so as to provide a notification that a detectable incidence of deception has likely already occurred as well as to provide a predictive notification that an indicia of deception may occur in the future. For example, the first threshold value may be a predictive threshold value indicating that a number or rate of indicia of deception has occurred which rise to a level which is not likely to be a detectable incidence of deception but may be trending towards such a level. The second threshold value may be a detectable threshold value indicating that sufficient number of indicia of deception have been present in communications content 102 that a content-receiving participant 109 may detect it as an incidence of deception.

It may be the case that the deceptive indicia detection module 115 and deceptive indicia notification module 128 may perform deceptive indicia detection and notification in a substantially real-time manner during a communication interaction (e.g. a video conference) between the content-generating participant 103 and the content-receiving participant 109 to allow the content-receiving participant 109 to monitor the communications content 102 for indicia of deception. Further, upon completion of a communications interaction, it may be advisable for a content-receiving participant 109 to review the communications content 102 and any detected indicia of deception for education and/or training purposes. As such, during a communication interaction, the deceptive indicia detection module 115 may record the communications content 102 and apply one or more tags to the recorded communications content 102 according to detected occurrences of indicia of deception.

For example, during a communication interaction, the deceptive indicia detection module 115 may detect an incidence of indicia of deception. The deceptive indicia detection module 115 may sample a portion of the communications content 102 containing the detected incidence of indicia of deception and store an audio/video file containing the sampled portion of the communications content 102 containing the detected incidence of indicia of deception to a deceptive indicia library database 129. The audio/video file containing the sampled portion of the communications content 102 containing the detected incidence of indicia of deception may be annotated with information regarding the indicia of deception (e.g. the type of indicia of deception, the degree of deception indicated, etc.) to facilitate review of the detected indicia of deception.

In another example, during a communication interaction, the deceptive indicia detection module 115 may detect an incidence of indicia of deception. The deceptive indicia detection module 115 may record the communications content 102 as an audio/video file and apply a graphical element (e.g. a "flag" icon 132) to the audio/video file at a time associated with the detection of an incidence of indicia of deception. The recorded audio/video file containing the graphical element communications content 102 associated with the detected incidence of indicia of deception may be stored to the deceptive indicia library database 129.

In another example, during a communication interaction, the deceptive indicia detection module 115 may detect an incidence of indicia of deception. The deceptive indicia detection module 115 may store a time stamp associated with the detected incidence of the indicia of deception to the deceptive indicia library database 129.

In another example, a content-receiving participant 109 may be independently aware of an occurrence of an indicia of deception contained in the communications content 102 (e.g. the content-receiving participant 109 knows the content-generating participant 103 has lied about a maximum authorized purchase price during a negotiation). In such a case, the communication content receiving system 106 may receive a user input via user input device 131 indicative of an occurrence of indicia of deception in the communications content 102. The deceptive indicia detection module 115 may correlate the occurrence of the user input to detected indicia of deception and apply a tag (e.g. an audio/video sample, an insertion of a graphical element, storing a time stamp, etc.) to the communications content 102 according to the user input.

Figure 3B:
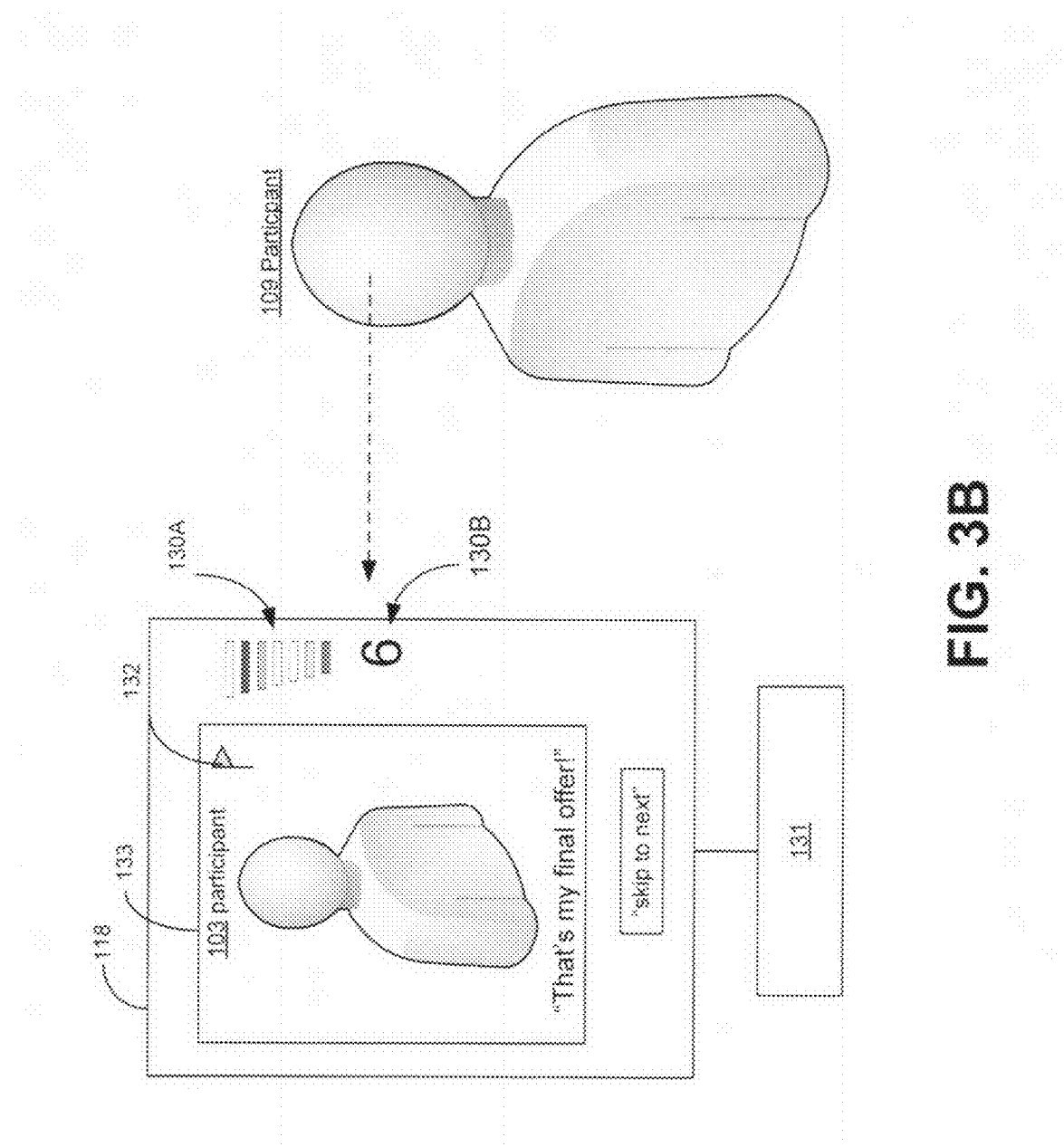
FIG. 3B shows an exemplary high-level block diagram of an exemplary system.

As described above, it may be advisable for a content-receiving participant 109 to review the communications content 102 and any detected indicia of deception for education and/or training purposes. As such, following tagging of the communications content 102 according to the detected indicia of deception, the portions of the communications content 102 associated with the tagged indicia of deception may be replayed to the content-receiving participant 109. For example, as shown in FIG. 3B, one or more tagged portions of the communications content 102 may be retrieved from the deceptive indicia library database 129 and displayed/broadcasted by the presentation module 108 via a review interface 133. The review interface 133 may include video playback functionality configured to present the communications content 102 according to the tags. For example, the review interface 133 may allow for the content-receiving participant 109 to skip to portions of the communications content 102 associated with the tags. For example, the review interface 133 may provide a "skip to next" user interface element whereby a user input associated with the "skip to next" user interface element causes the review interface 133 to display/broadcast the next instance of the communications content 102 having a tag associated with a detection of indicia of deception.

Further, it may be the case that the content-receiving participant 109 may suspect that the content-generating participant 103 may be employing indicia of deception masking techniques via deceptive indicia masking module 126. As such, the communication content receiving system 106 may further include a deceptive indicia masking detection module 134. The deceptive indicia masking detection module 134 may receive modified communications content 102' and detect whether or not deceptive indicia masking has been applied to the original communications content 102. Upon detection of one or more instances of deceptive indicia masking by the deceptive indicia masking detection module 134, the deceptive indicia masking detection module 134 may remove the instances of the deceptive indicia masking from the modified communications content 102' to restore the original communications content 102 and provide the original communications content 102 and/or a notification that deceptive indicia masking has been detected to the content-receiving participant 109 via the presentation module 108.

Still further, it may be the case that multiple content-receiving participants 109 may employ multiple communication content receiving systems 106 to receive communications content 102 from a common content-generating participant 103. In order to generate a more comprehensive indicia of deception profile for the content-generating participant 103, the content-receiving participants 109 may aggregate their respective indicia of deception data in a deceptive indicia repository 135 that is commonly accessible by the content-receiving participants 109. For example, each communication content receiving system 106 may upload indicia of deception data associated with one or more communication interactions with the content-generating participant 103 to the deceptive indicia repository 135. Further, each communication content receiving system 106 may download aggregated indicia of deception data associated with multiple communication interactions with the content-generating participant 103 to and provide that aggregated indicia of deception data to a content-receiving participant 109 via the presentation module 108 for review by the content-receiving participant 109.

Figure 2B:
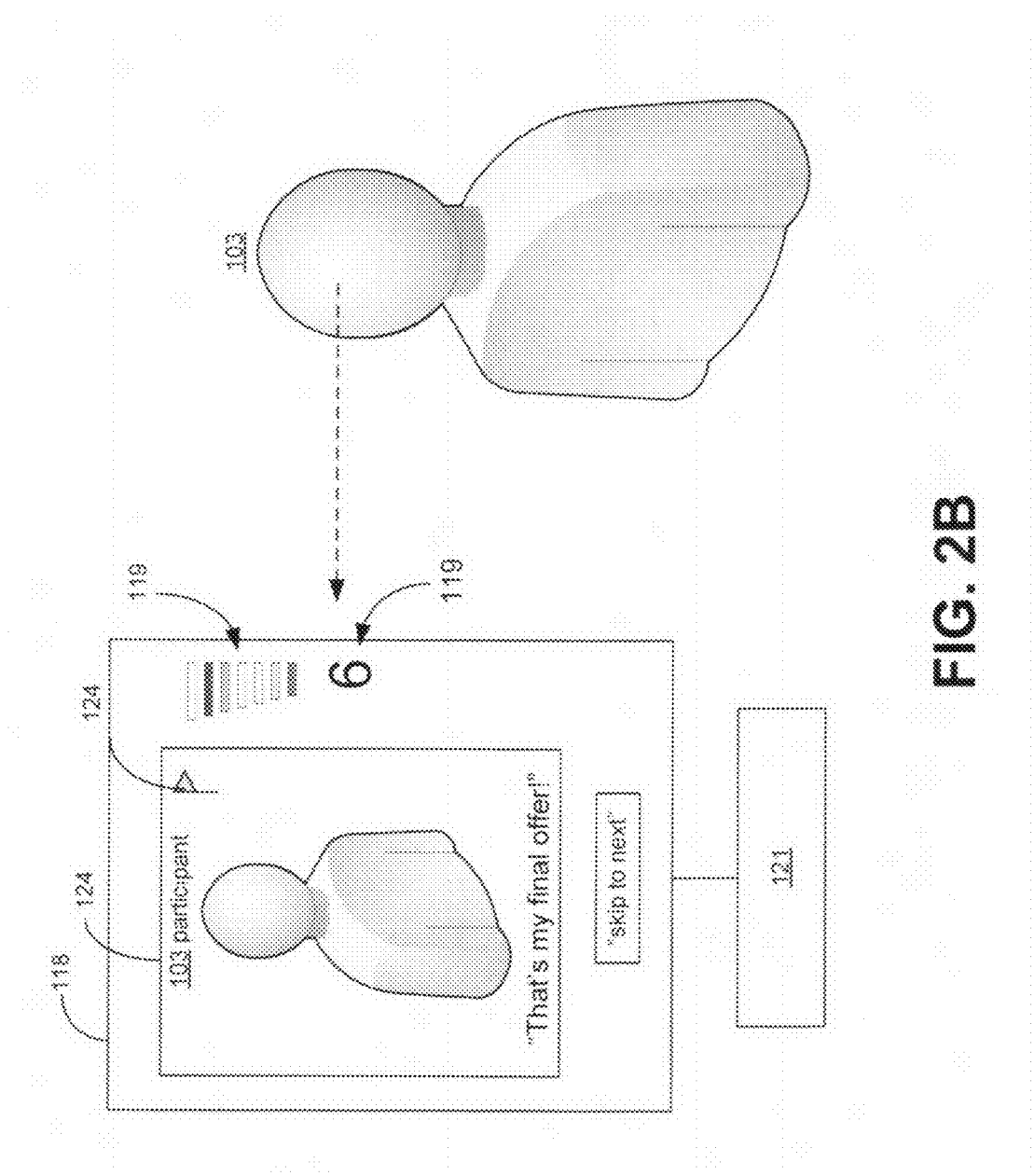
FIG. 2B shows an exemplary high-level block diagram of an exemplary system.
Figure 4:
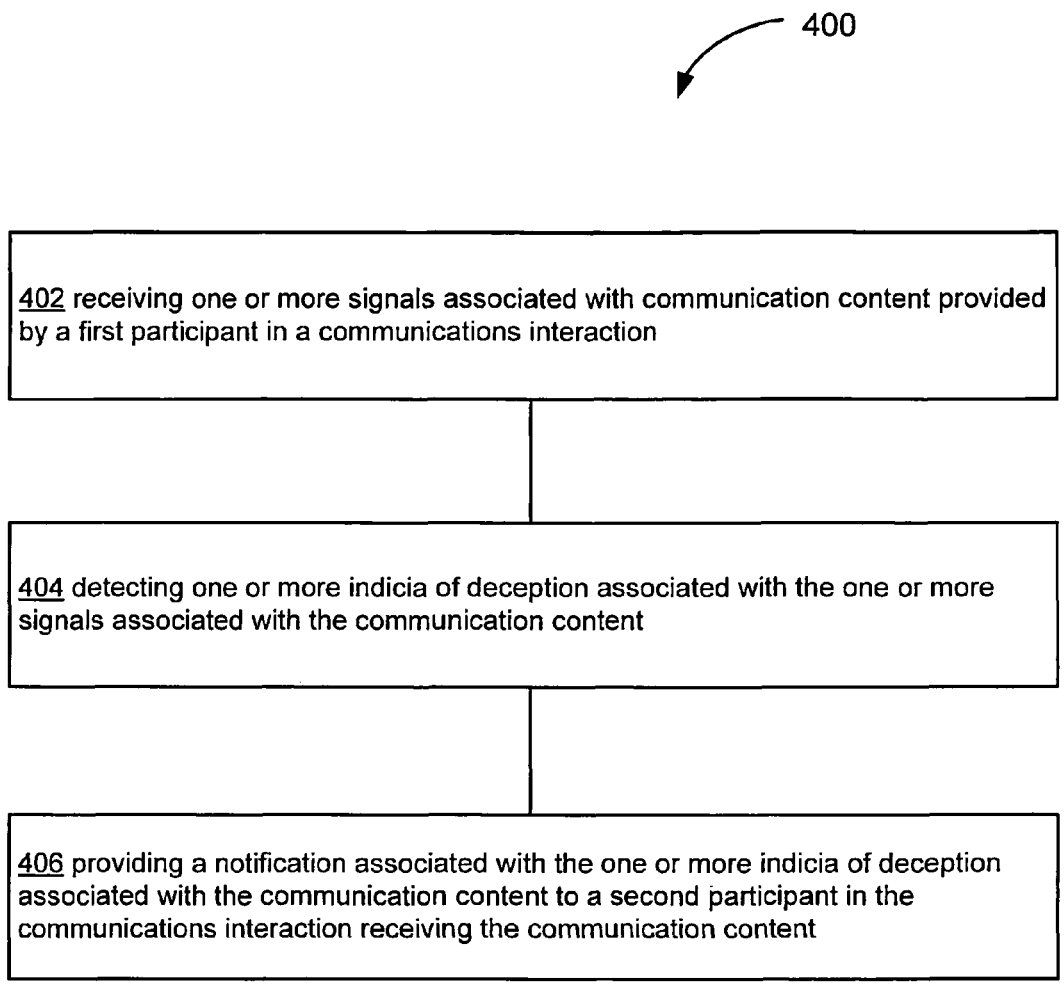
FIG. 4 shows an operational procedure.

FIG. 4 and the following figures include various examples of operational flows, discussions and explanations may be provided with respect to the above-described exemplary environment of FIGS. 1-3. However, it should be understood that the operational flows may be executed in a number of other environments and contexts, and/or in modified versions of FIGS. 1-3. Also, although the various operational flows are presented in the sequence(s) illustrated, it should be understood that the various operations may be performed in different sequential orders other than those which are illustrated, or may be performed concurrently.

Further, in the following figures that depict various flow processes, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

FIG. 4 illustrates an operational procedure 400 for practicing aspects of the present disclosure including operations 402, 404 and 406.

Operation 402 illustrates receiving one or more signals associated with communication content provided by a first participant in a communications interaction. For example, as shown in FIG. 1, For example, as shown in FIG. 1, a communications content transmitting system 100 may include a communications content capture device 101. The communications content capture device 101 may include, but is not limited to, a video capture device (e.g. a digital camera, web cam, teleconferencing camera, etc.), an audio capture device (e.g. a microphone, telephone), and the like. The communications content 102 received by the communication content receiving system 106 from the communications content transmitting system 100 via the communications module 107 may be provided to the deceptive indicia detection module 115 for analysis of the communications content 102 to determine if the communications content 102 represents an indicia of deception. For example, the audio and/or video of the communications content 102 may be analyzed to determine the various physiological characteristics such as heart rate, blood pressure, breathing patterns, perspiration levels as well as other parameters such as eye dilation, eye movements, voice stress, language constructs, and the like of the content-generating participant 103.

Operation 404 illustrates detecting one or more indicia of deception associated with the one or more signals associated with the communication content. For example, as shown in FIG. 1, upon receipt of communications content 102 received from the communications content capture device 101, such data may be analyzed by the deceptive indicia detection module 115 for correspondence with one or more defined deceptive indicia threshold values maintained in the deceptive indicia threshold database 127. Exceeding one or more deceptive indicia threshold values may be an indicator that the content-generating participant 103 is presenting one or more physiological indicators, speech patterns and/or physical movements that may be associated with deception in the communications content 102.

Operation 406 illustrates providing a notification associated with the one or more indicia of deception associated with the communication content to a second participant in the communications interaction receiving the communication content. For example, as shown in FIGS. 1 and 3A-3B, in a case where a content-generating participant 103 is presenting one or more indicia of deception (e.g. physiological indicators, speech patterns and/or physical movements), it may be desirable for the content-receiving participant 109 be made aware of indicia of deception in the communications content 102 so that the content-receiving participant 109 may properly account for such indicia in judging the veracity of the communications content 102. As such, the communication content receiving system 106 may include a deceptive indicia notification module 128. The deceptive indicia notification module 128 may receive one or more signals from the deceptive indicia detection module 115 indicating the presence or absence of deceptive indicia in communications content 102 being provided to the content-receiving participant 109. Upon the receipt of one or more signals associated with the presence of indicia of deception in communications content 102 from the deceptive indicia detection module 115, the deceptive indicia notification module 128 may, in turn provide one or more signals to a presentation module 108 so that an indicator associated with the indicia of deception is presented to the content-receiving participants 109.

Figure 5:
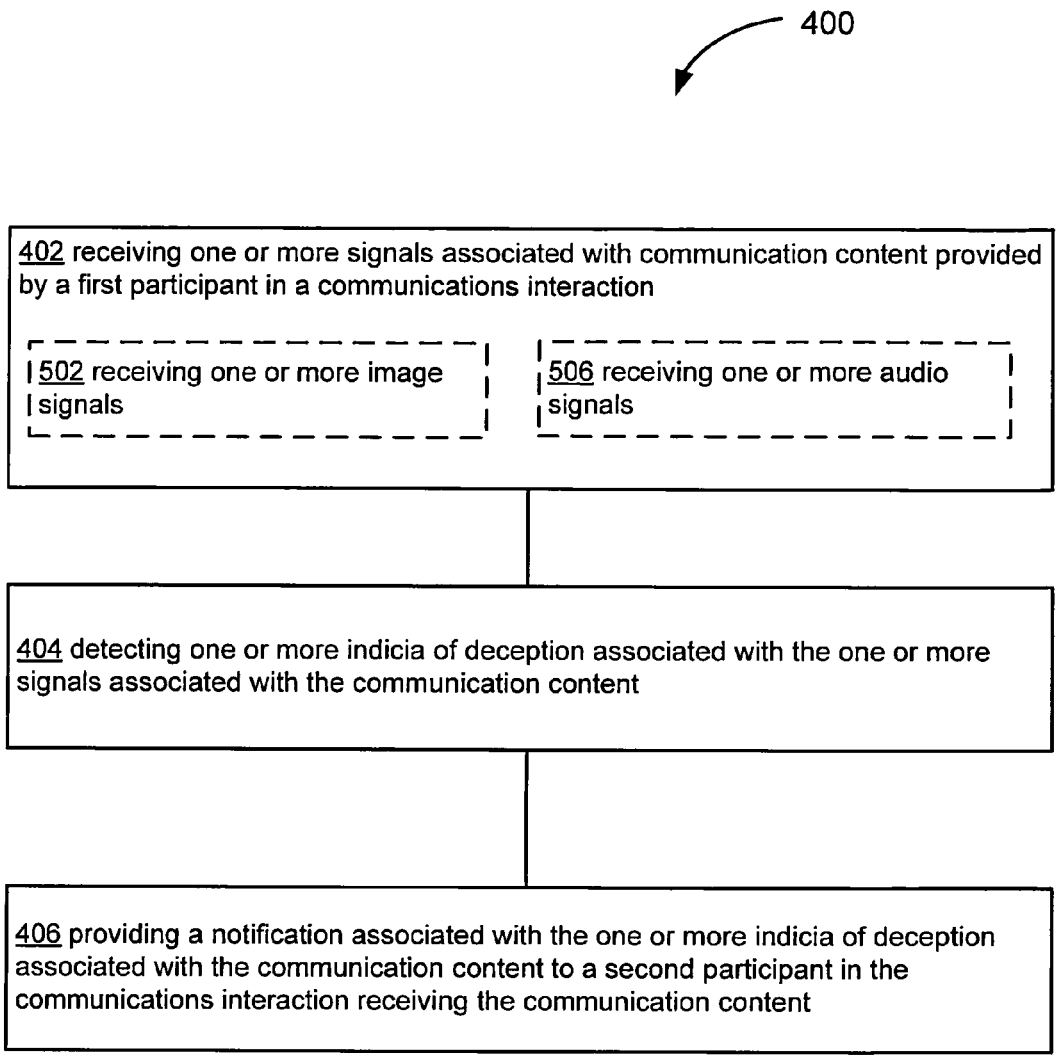
FIG. 5 shows an alternative embodiment of the operational procedure of FIG. 4.

FIG. 5 illustrates an example embodiment where the operation 402 of example operational flow 400 of FIG. 4 may include at least one additional operation. Additional operations may include an operation 502, 504, 506 and/or 508.

Operation 502 illustrates receiving one or more image signals. For example, as shown in FIG. 1, the communications content capture device 101 may include a high-resolution camera (e.g. a camera having a resolution of at least 720 lines in a vertical direction). A high-resolution camera image may include sufficient resolution to externally image the movement of one or more blood vessels (e.g. the external carotid artery, external jugular vein, superficial temporal artery, etc.) of the content-generating participant 103. The deceptive indicia detection module 115 may receive signals indicative of the blood vessel image and acquire measurements (e.g. pixel counts, reflectivity fluctuations, color, etc. in the blood vessel image) representing the various changes in size of the blood vessel over a period of time indicating one or more heart beats. Such measurements over time may be used to compute a heart rate for the content-generating participant 103. The computed heart rate may be compared to a deceptive indicia threshold value maintained in the deceptive indicia threshold database 127. As an elevated heart rate may be an indicator of stress associated with providing deceptive communications content 102, a computed heart rate in excess of the deceptive indicia threshold value may be detected as indicia of deception in the communications content 102.

In another exemplary embodiment, the high-resolution camera may image the skin surface of the content-generating participant 103. The deceptive indicia detection module 115 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

In another exemplary embodiment, the high-resolution camera may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored over time. For example, in the case of a right-handed person, movement of the eyes to the up and left may be indicative of a "constructed" response which may be indicative of deception.

Further, certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

Operation 504 illustrates receiving one or more audio signals. For example, as shown in FIG. 1, the communications content capture device 101 may include a microphone. The microphone may capture an audio signal (e.g. speech content, a voice print, breathing, ambient noise, etc.) of the content-generating participant 103. The deceptive indicia detection module 115 may then analyze the audio signal and detect one or more characteristics of the audio signal.

Figure 6:
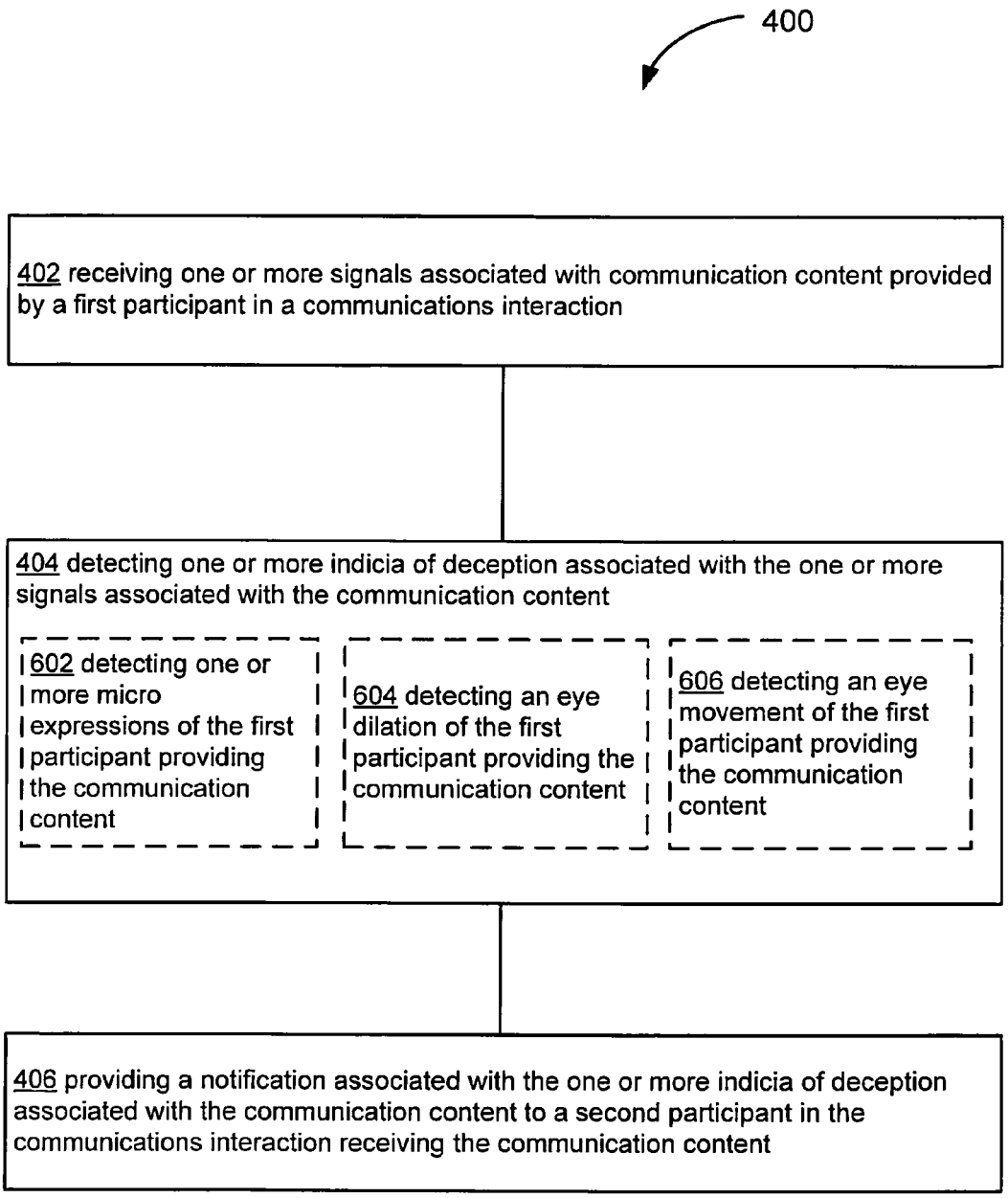
FIG. 6 shows an alternative embodiment of the operational procedure of FIG. 4.

FIG. 6 illustrates an example embodiment where the operation 404 of example operational flow 400 of FIG. 4 may include at least one additional operation. Additional operations may include an operation 602, 604 and/or 606.

Operation 602 illustrates detecting one or more micro expressions of the first participant providing the communication content. For example, as shown in FIG. 1, the high-resolution camera of the communications content capture device 101 may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. Certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

Operation 604 illustrates detecting an eye dilation of the first participant providing the communication content. For example, as shown in FIG. 1, the high-resolution camera of the communications content capture device 101 may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time.

Operation 606 illustrates detecting an eye movement of the first participant providing the communication content. For example, as shown in FIG. 1, the high-resolution camera may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception.

Figure 7:
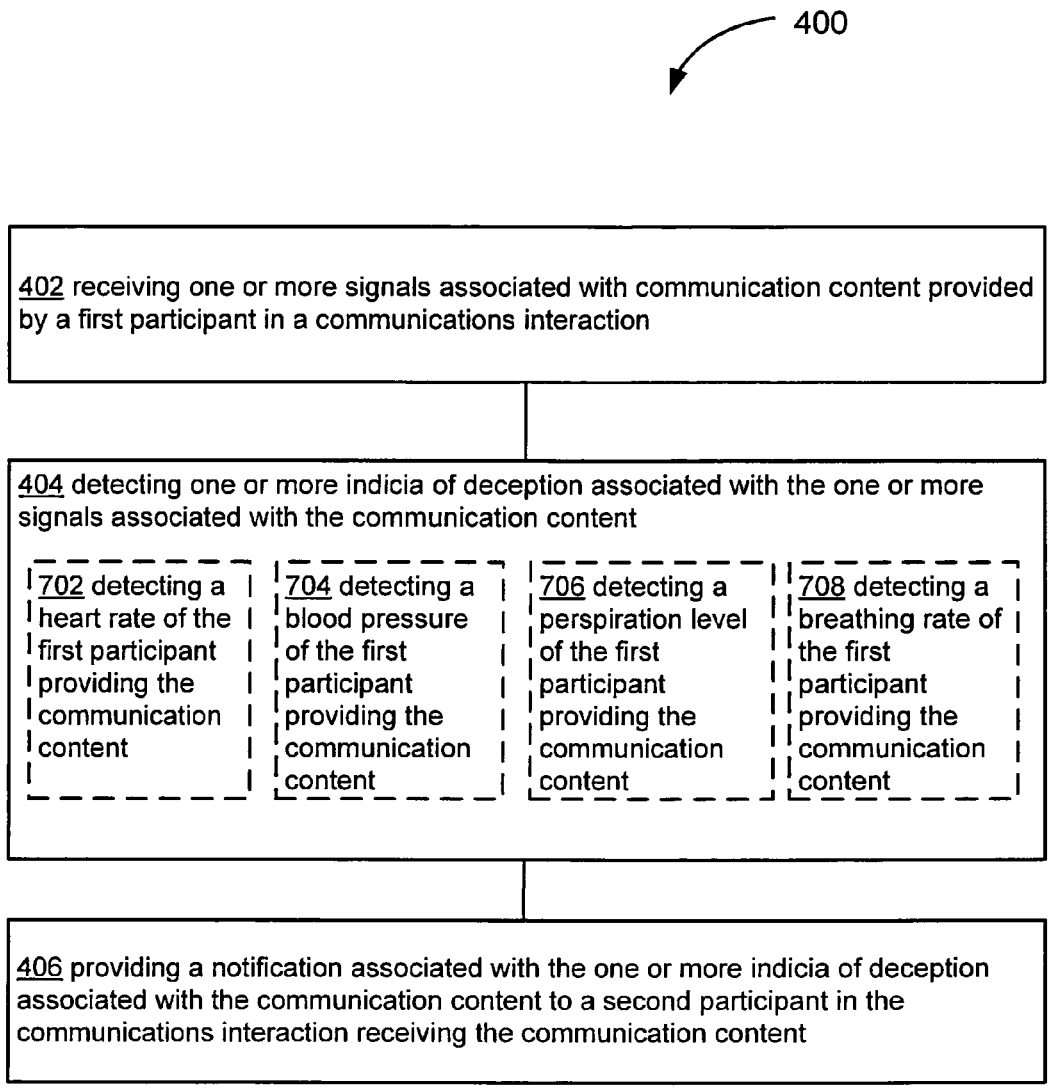
FIG. 7 shows an alternative embodiment of the operational procedure of FIG. 4.

FIG. 7 illustrates an example embodiment where the operation 404 of example operational flow 400 of FIG. 4 may include at least one additional operation. Additional operations may include an operation 702, 704, 706 and/or operation 708.

Operation 702 illustrates detecting a heart rate of the first participant providing the communication content. For example, as shown in FIG. 1, the high-resolution camera of the communications content capture device 101 may externally image one or more blood vessels of the content-generating participant 103. The deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate. The computed heart rate may be compared to a deceptive indicia threshold value maintained in the deceptive indicia threshold database 114. As an elevated heart rate may be an indicator of stress associated with providing deceptive communications content 102, a computed heart rate in excess of the deceptive indicia threshold value may be detected as indicia of deception in the communications content 102.

Operation 704 illustrates detecting a blood pressure of the first participant providing the communication content. For example, as shown in FIG. 1, the high-resolution camera of the communications content capture device 101 may externally image one or more blood vessels of the content-generating participant 103. The deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102.

Operation 706 illustrates detecting a perspiration level of the first participant providing the communication content. For example, as shown in FIG. 1, the high-resolution camera of the communications content capture device 101 may image the skin surface of the content-generating participant 103. The deceptive indicia detection module 115 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

Operation 708 illustrates detecting a breathing rate of the first participant providing the communication content. For example, as shown in FIG. 1, the communications content capture device 101 and/or the physiological data capture device 112 may include a high-resolution camera. The high-resolution camera may image the skin surface of the content-generating participant 103. The deceptive indicia detection module 115 may receive signals associated with the image of the content-generating participant 103 and detect the locations of one or more bodily features. The relative positions of such bodily features may be measured (e.g. pixel counts in the skin surface image) and monitored for changes over time. For example, movement of various bodily features (e.g. the expansion and contraction of the chest cavity, movement of the shoulders, etc.) may be indicative of respiration. As an elevated level of rate of respiration may be an indicator of stress associated with providing deceptive communications content 102, a computed breathing rate in excess of the deceptive indicia threshold value (e.g. a breathing rate) may be detected as indicia of deception in the communications content 102.

Figure 8:
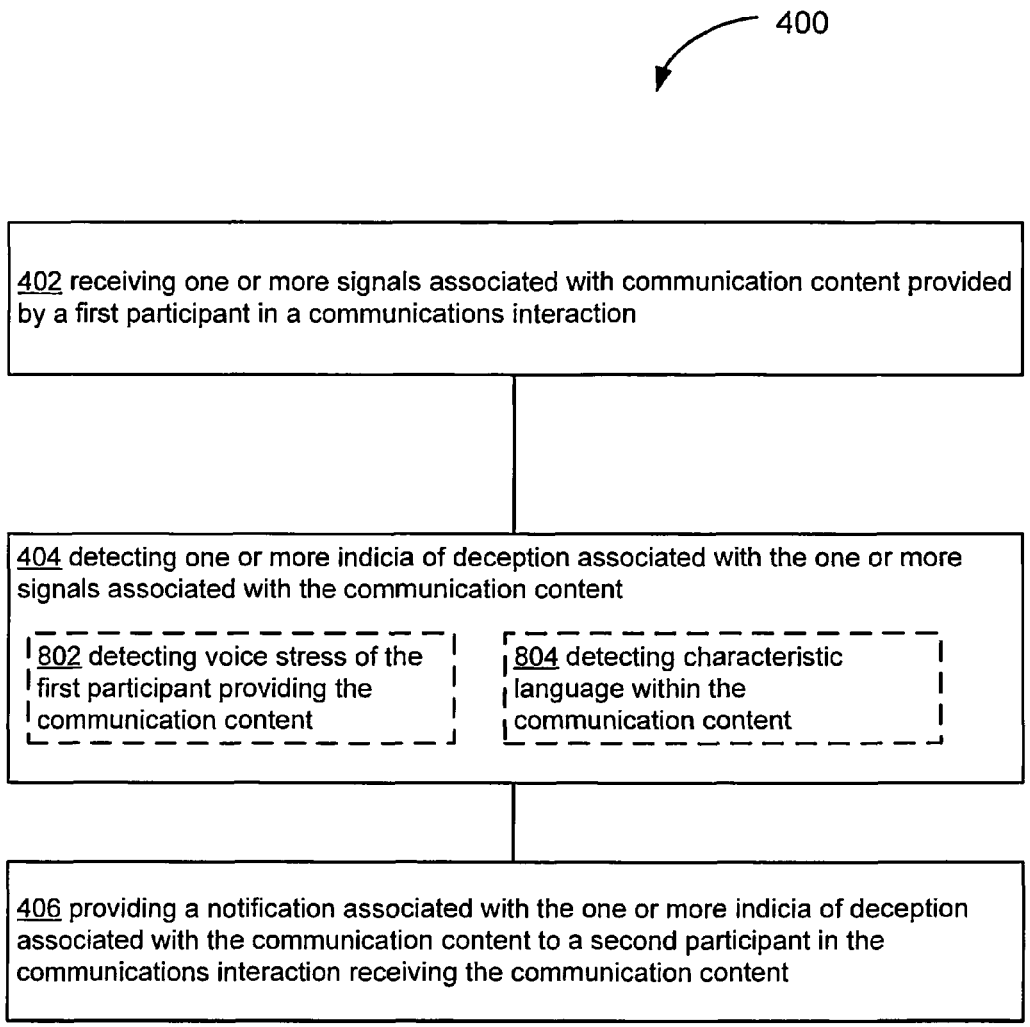
FIG. 8 shows an alternative embodiment of the operational procedure of FIG. 4.

FIG. 8 illustrates an example embodiment where the operation 404 of example operational flow 400 of FIG. 4 may include at least one additional operation. Additional operations may include an operation 802 and/or operation 804.

Operation 802 illustrates detecting voice stress of the first participant providing the communication content. For example, as shown in FIG. 1, the deceptive indicia detection module 115 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 115 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102.

Operation 804 illustrates detecting characteristic language within the communication content. For example, the communications content capture device 101 may include a microphone. The microphone may capture speech content of the content-generating participant 103. The deceptive indicia detection module 115 may then analyze the audio signal and detect one or more characteristics of the audio signal. For example, the deceptive indicia detection module 115 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "I thought . . . " instead of "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 115 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102.

Figure 9:
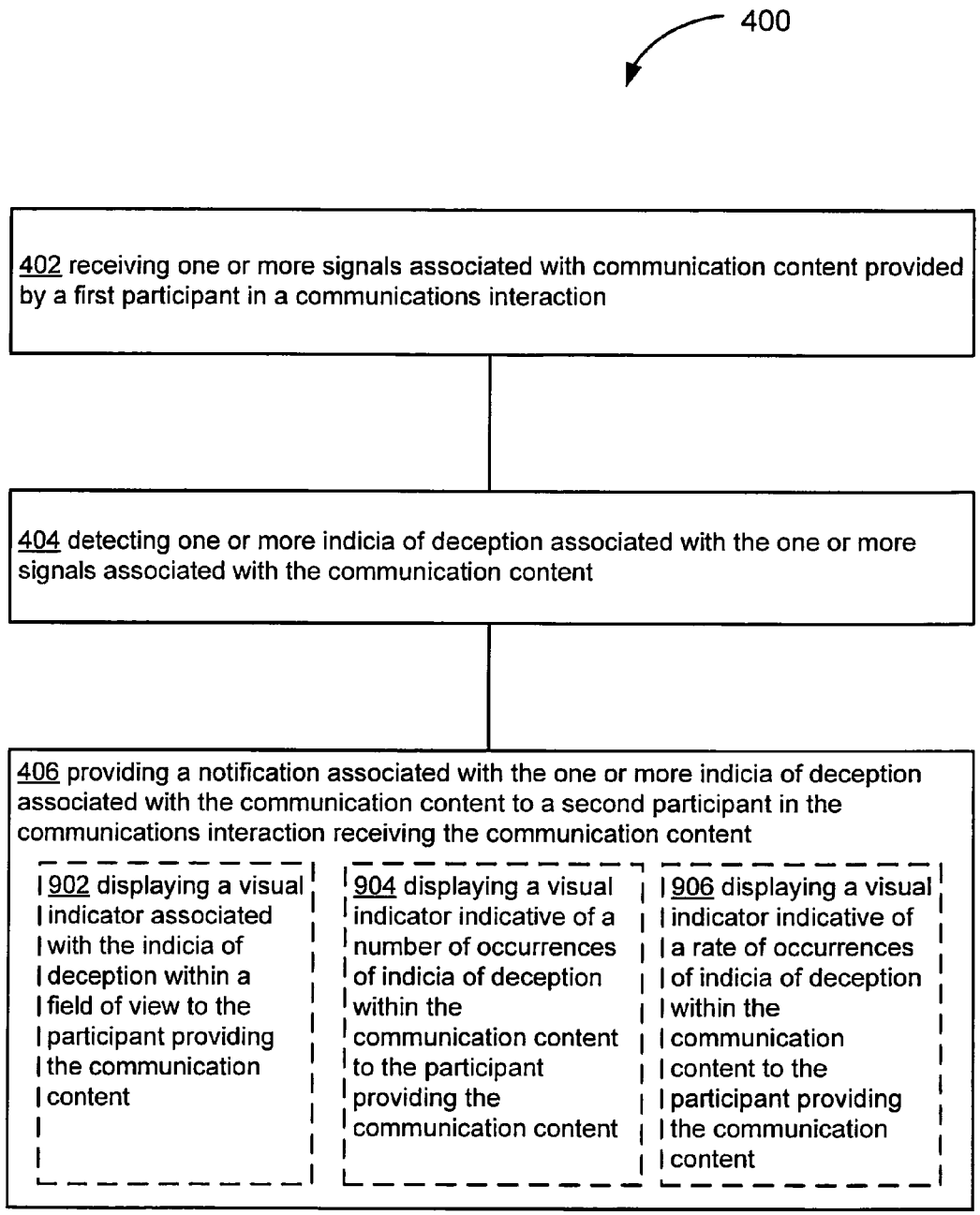
FIG. 9 shows an alternative embodiment of the operational procedure of FIG. 4.

FIG. 9 illustrates an example embodiment where the operation 406 of example operational flow 400 of FIG. 4 may include at least one additional operation. Additional operations may include an operation 902, 904 and/or operation 906.

Operation 902 illustrates displaying a visual indicator associated with the indicia of deception within a field of view to the second participant receiving the communication content. For example, as shown in FIGS. 1 and 3A-3B, upon the receipt of one or more signals associated with the presence of indicia of deception in communications content 102 from the deceptive indicia detection module 115, the deceptive indicia notification module 128 may provide one or more video signals to a display device 110 (e.g. an LCD display) so that a visual indicator 130 associated with the indicia of deception is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may further display the visual indicator 130 (e.g. a color coded indicator) that presents a cumulative number of occurrences of indicia of deception in the communications content 102, a rate of occurrences of indicia of deception in the communications content 102, and the like. The visual indicator 130 may be a dynamic indicator that changes (e.g. moves from an indicated "high" rate of indicia of deception to an indicated "low" rate of indicia of deception) in real-time according to the type and/or amount of indicia of deception detected within communications content 102.

Operation 904 illustrates displaying a visual indicator indicative of a number of occurrences of indicia of deception within the communication content to the second participant receiving the communication content. For example, as shown in FIGS. 1 and 3A-3B, upon the receipt of one or more signals associated with the presence of indicia of deception in communications content 102 from the deceptive indicia detection module 115, the deceptive indicia notification module 128 may provide one or more video signals to a display device 110 (e.g. an LCD display) so that a visual indicator 130 associated with the indicia of deception is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may display a visual indicator 130B that presents a cumulative number of occurrences of indicia of deception in the communications content 102.

Operation 906 illustrates displaying a visual indicator indicative of a rate of occurrences of indicia of deception within the communication content to the second participant receiving the communication content. For example, as shown in FIGS. 1 and 3A-3B, upon the receipt of one or more signals associated with the presence of indicia of deception in communications content 102 from the deceptive indicia detection module 115, the deceptive indicia notification module 128 may provide one or more video signals to a display device 110 (e.g. an LCD display) so that a visual indicator 130 associated with the indicia of deception is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may display a visual indicator 130A that presents a rate of occurrences of indicia of deception in the communications content 102. The visual indicator 130 may be a dynamic indicator that changes (e.g. moves from an indicated "high" rate of indicia of deception to an indicated "low" rate of indicia of deception) in real-time according to the type and/or amount of indicia of deception detected within communications content 102.

Figure 10:
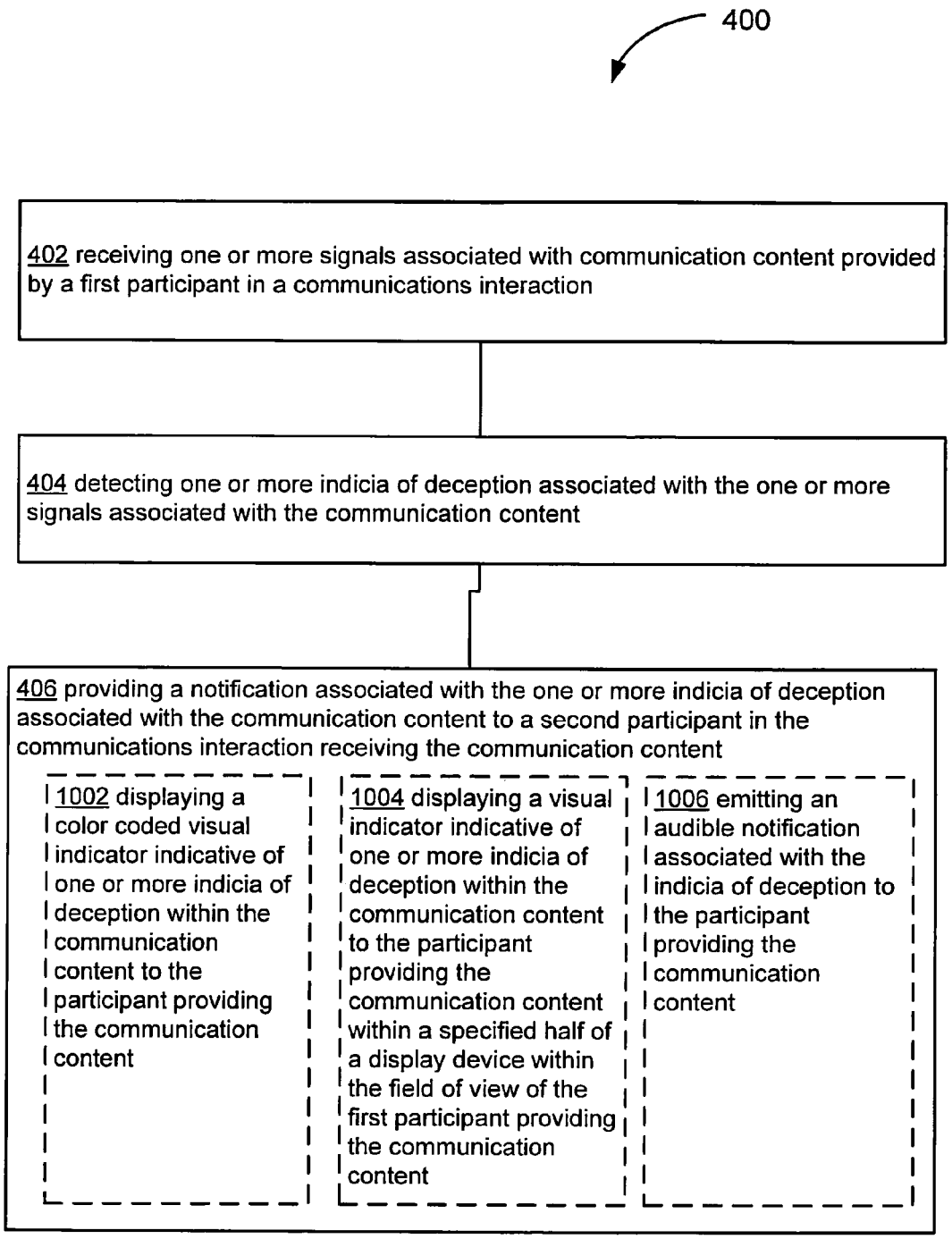
FIG. 10 shows an alternative embodiment of the operational procedure of FIG. 4.

FIG. 10 illustrates an example embodiment where the operation 406 of example operational flow 400 of FIG. 4 may include at least one additional operation. Additional operations may include an operation 1002, 1004 and/or operation 1006.

Operation 1002 illustrates displaying a color coded visual indicator indicative of one or more indicia of deception within the communication content to the second participant receiving the communication content. For example, as shown in FIGS. 1 and 3A-3B, upon the receipt of one or more signals associated with the presence of indicia of deception in communications content 102 from the deceptive indicia detection module 115, the deceptive indicia notification module 128 may provide one or more video signals to a display device 110 (e.g. an LCD display) so that a visual indicator 130 associated with the indicia of deception is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may display a color coded visual indicator 130A (e.g. "green" level indicating a low rate of occurrences of indicia of deception, a "yellow" level indicating a moderate rate of occurrences of indicia of deception, to a "red" level indicating a high rate of occurrences of indicia of deception). The visual indicator 130A may be a dynamic indicator that changes (e.g. moves from an indicated "high" rate of indicia of deception to an indicated "low" rate of indicia of deception) in real-time according to the type and/or amount of indicia of deception detected within communications content 102. Alternately, each indicia of deception type may be represented by a separate visual indicator 130 having a designated color. For example, eye movement indicia of deception may be represented by a blue visual indicator 130 while formal language indicia of deception may be represented by a green visual indicator 130.

Operation 1004 illustrates displaying a visual indicator indicative of one or more indicia of deception within the communication content to the second participant receiving the communication content within a specified half of a display device within the field of view of the second participant receiving the communication content. For example, as shown in FIGS. 1 and 3A-3B, upon the receipt of one or more signals associated with the presence of indicia of deception in communications content 102 from the deceptive indicia detection module 115, the deceptive indicia notification module 128 may provide one or more video signals to a display device 110 (e.g. an LCD display) so that a visual indicator 130 associated with the indicia of deception is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may display a visual indicator 130 that presents a rate of occurrences of indicia of deception in the communications content 102, a cumulative number of occurrences of indicia of deception in the communications content 102, and the like. Further, it will be noted that certain eye movements may be indicia of deception. For example, in the case of a right-handed person, movement of the eyes to the up and left may be indicative of a "constructed" response which may be indicative of deception. Conversely, movement of the eyes up and to the right may be indicative of a "memory recall" response which may be indicative of truthfulness. The above referenced conventions may be reversed for a left-handed person. As such, the communications content transmitting system 100 may further include a user input device 121 (e.g. a keyboard, mouse, touch pad, touch screen, etc.) that may receive a user input from the content-receiving participant 109 specifying a "handedness" of the content-generating participant 103. The visual indicator 130 may be displayed on the display device 110 according to the specified "handedness" of the content-receiving participant 109 so that the act of looking at the visual indicator 130 by the content-receiving participant 109 during a communications interaction is not, itself, an indicia of deception by the content-receiving participant 109. Specifically, for a right-handed content-receiving participant 109, the visual indicator 130 may be displayed on the right-hand half of the display device 110. For a left-handed content-receiving participant 109, the visual indicator 130 may be displayed on the left-hand half of the display device 110 (not shown).

Operation 1006 illustrates emitting an audible notification associated with the indicia of deception to the second participant receiving the communication content. For example, as shown in FIG. 1, upon the receipt of one or more signals associated with the presence of indicia of deception in communications content 102 from the deceptive indicia detection module 115, the deceptive indicia notification module 128 may provide one or more audio signals to an audio speaker 111 (e.g. an audio speaker, headset, earpiece, etc.) that an audio indicator (e.g. a notification sound effect such as a beep, a spoken message, etc.) associated with the indicia of deception is emitted to the content-receiving participant 109.

Figure 11:
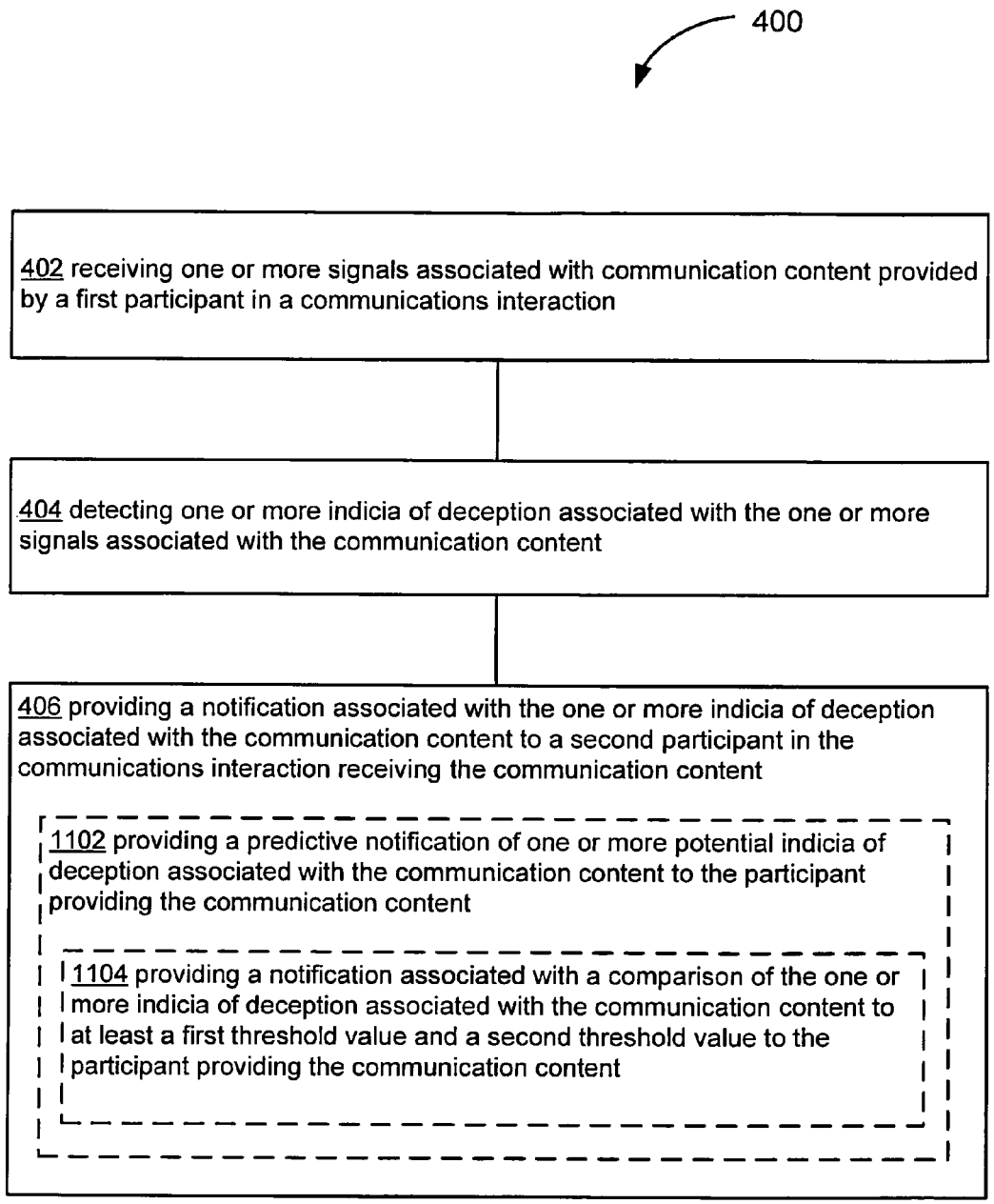
FIG. 11 shows an alternative embodiment of the operational procedure of FIG. 4.

FIG. 11 illustrates an example embodiment where the operation 406 of example operational flow 400 of FIG. 4 may include at least one additional operation. Additional operations may include an operation 1102 and/or operation 1104.

Operation 1102 illustrates providing a predictive notification of one or more potential indicia of deception associated with the communication content to the second participant receiving the communication content. For example, as shown in FIGS. 1 and 3A-3B, in order to anticipate the presentation of a deceptive statement by the content-receiving participant 109, the deceptive indicia detection module 115 may detect indicia of deception which do not rise to a level associated with actual deception but instead, may be indicative that a potential deceptive statement may occur in the near future. As such, the deceptive indicia detection module 115 provide a predictive notification to the content-receiving participant 109 that the level of indicia of deception present in the communications content 102 is approaching levels that may eventually indicate an actual deceptive statement.

Operation 1104 illustrates providing a notification associated with a comparison of the one or more indicia of deception associated with the communication content to at least a first threshold value and a second threshold value to the second participant receiving the communication content. For example, as shown in FIGS. 1 and 3A-3B, the deceptive indicia detection module 115 may maintain two or more threshold values associated with a given indicia of deception (e.g. eye movement, characteristic language, etc.) in deceptive indicia threshold database 114 so as to provide a predictive notification that an indicia of deception may occur in the future or that that a detectable incidence of deception has likely occurred. For example, the first threshold value may be a predictive threshold value indicating that a threshold number or rate of indicia of deception has occurred which rise to a level which does not indicate actual deception but may be trending towards such a level. The second threshold value may be a detectable threshold value indicating that a sufficient number of indicia of deception have detected in the communications content 102 to indicate a deceptive statement has occured.

Figure 12:
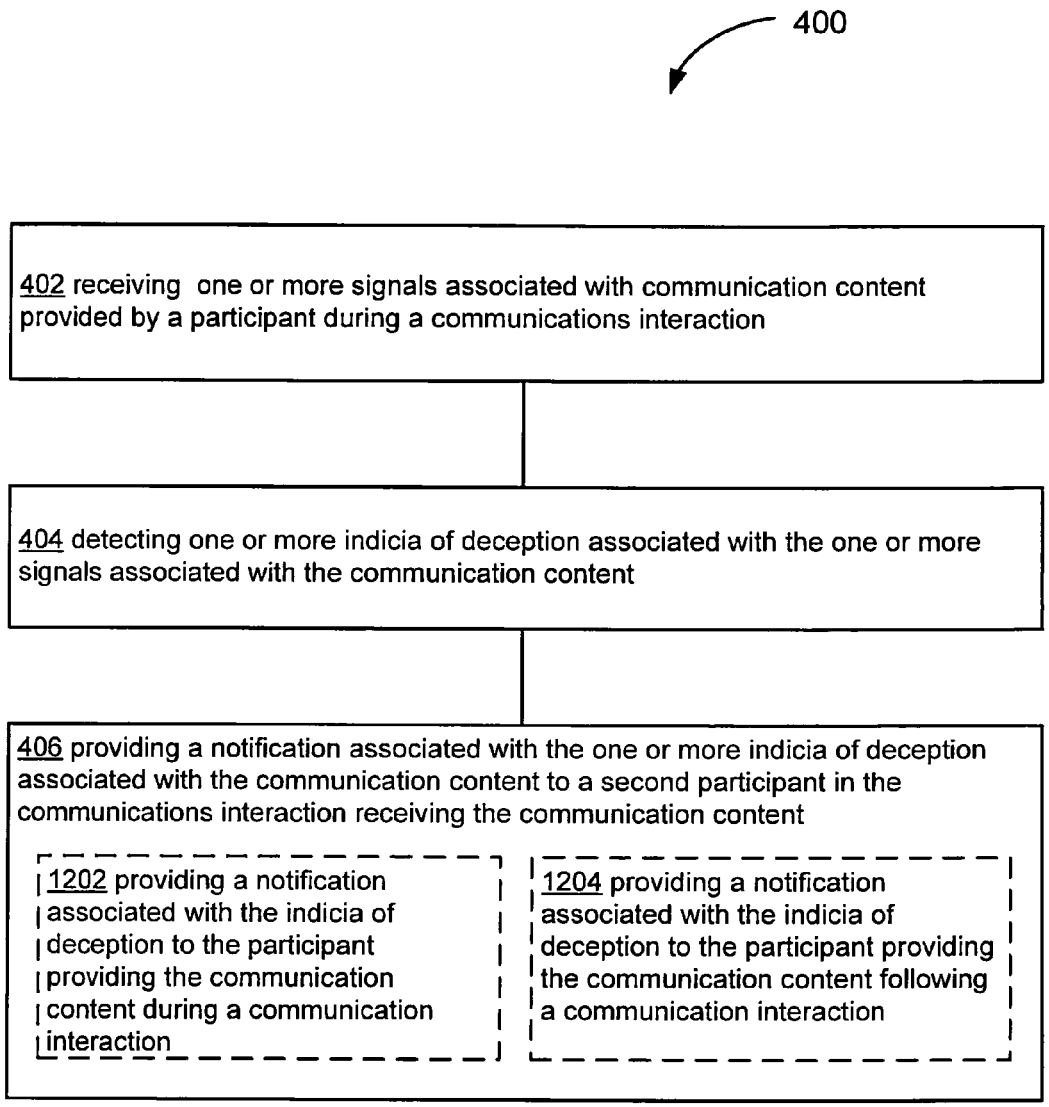
FIG. 12 shows an alternative embodiment of the operational procedure of FIG. 4.

FIG. 12 illustrates an example embodiment where the operation 406 of example operational flow 400 of FIG. 4 may include at least one additional operation. Additional operations may include an operation 1202 and/or operation 1204.

Operation 1202 illustrates providing a notification associated with the indicia of deception to the second participant receiving the communication content during a communication interaction. For example, as shown in FIGS. 1 and 3A, it may be the case that the deceptive indicia detection module 115 and deceptive indicia notification module 128 may perform deceptive indicia detection and notification (as described above) in a substantially real-time manner during a communication interaction (e.g. a video conference) between the content-generating participant 103 and the content-receiving participant 109 to allow the content-receiving participant 109 to monitor the communications content 102 for indicia of deception and account for such indicia of deception in their consideration of the veracity of the communications content 102 received from the content-generating participant 103.

Operation 1204 illustrates providing a notification associated with the indicia of deception to the second participant receiving the communication content following a communication interaction. For example, as shown in FIGS. 1 and 3B, upon completion of a communications interaction, it may be advisable for a content-receiving participant 109 to review the communications content 102 and any detected indicia of deception for education and/or training purposes. During a communication interaction, the deceptive indicia detection module 115 may detect an incidence of indicia of deception. The deceptive indicia detection module 115 may store a record associated with the detected indicia of deception to a deceptive indicia library database 129. Following the communications interaction, one or more portions of the communications content 102 may be retrieved from the deceptive indicia library database 129 and displayed/broadcasted by the presentation module 108 via a review interface 133. The review interface 133 may include video playback functionality configured to present the communications content 102 according to the records associated with the detected indicia of deception. The review interface 133 may allow for the content-generating participant 103 to skip to portions of the communications content 102 associated with the records associated with the detected indicia of deception. For example, the review interface 133 may provide a "skip to next" user interface element whereby a user input associated with the "skip to next" user interface element causes the review interface 133 to display/broadcast the next instance of the communications content 102 having a record associated with a detection of indicia of deception.

Figure 13:
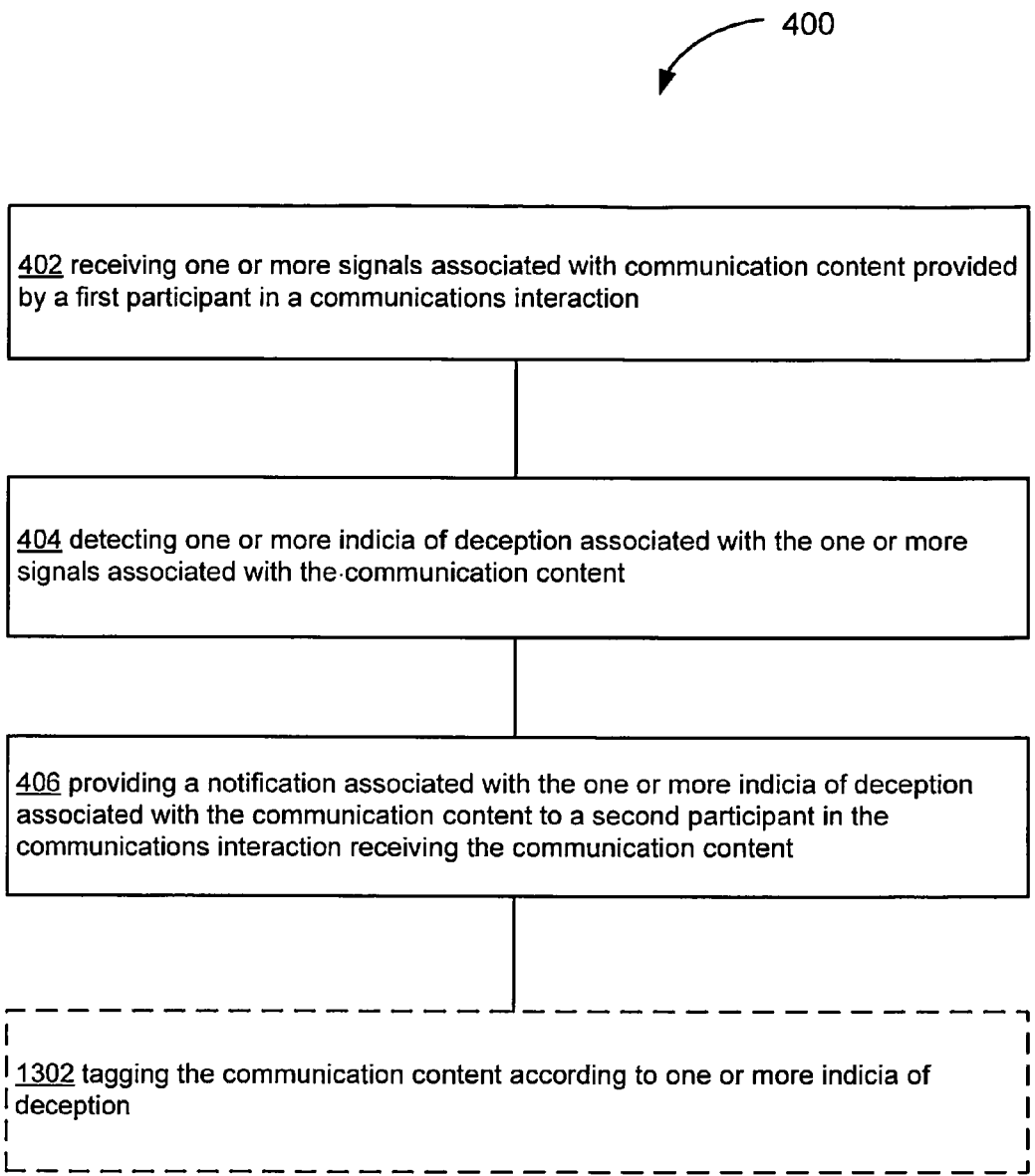
FIG. 13 shows an alternative embodiment of the operational procedure of FIG. 4.

FIG. 13 illustrates an example embodiment where the example operational flow 400 of FIG. 4 may include at least one additional operation. Additional operations may include an operation 1302.

Operation 1302 illustrates tagging the communication content according to one or more indicia of deception. For example, as shown in FIGS. 1 and 3B, upon completion of a communications interaction, it may be advisable for a content-generating participant 103 to review the communications content 102 and any detected indicia of deception for education and/or training purposes. During a communication interaction, the deceptive indicia detection module 115 may detect an incidence of indicia of deception. The deceptive indicia detection module 115 may record the communications content 102 and apply one or more tags to the recorded communications content 102 according to detected occurrences of indicia of deception.

Figure 14:
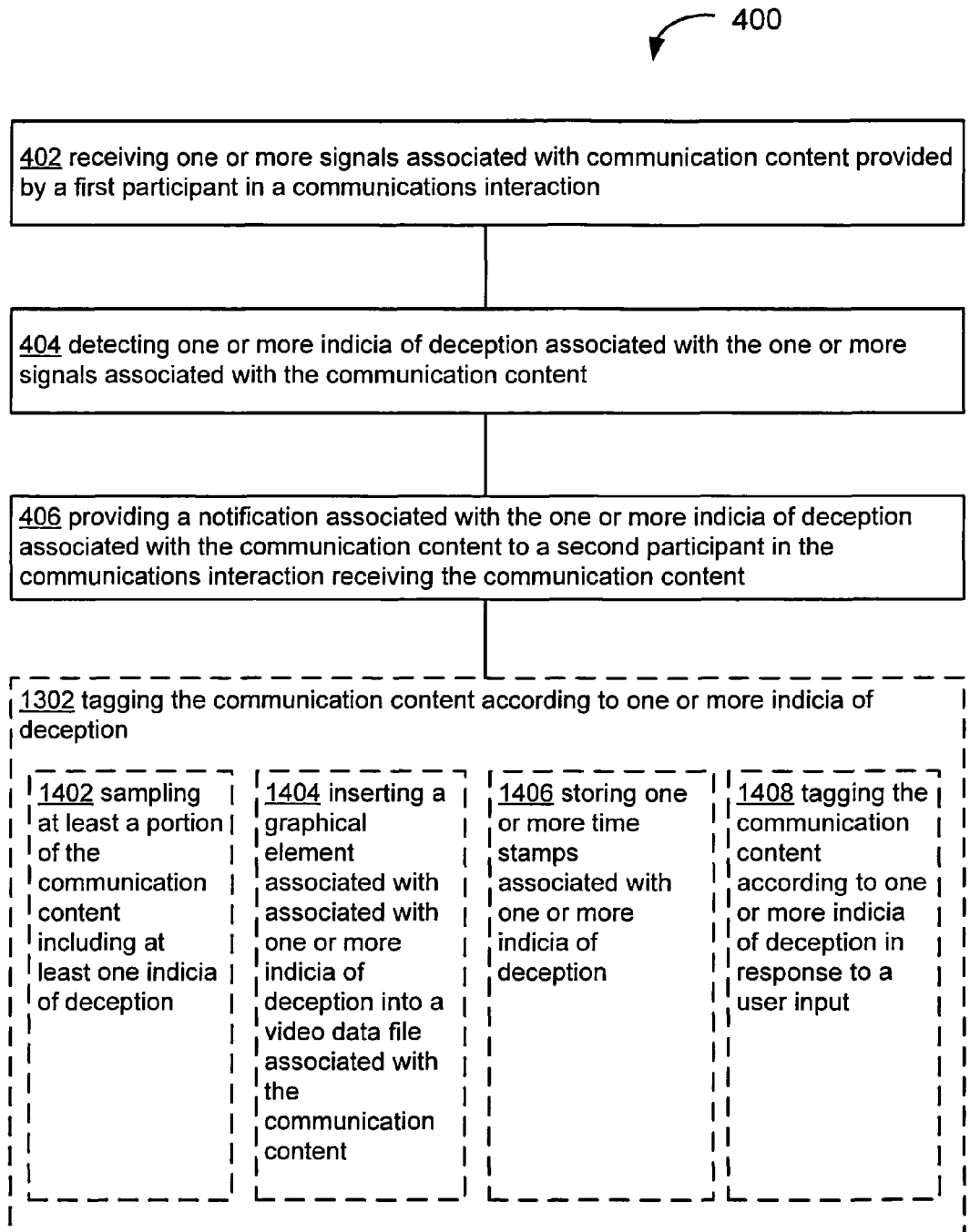
FIG. 14 shows an alternative embodiment of the operational procedure of FIG. 4.

FIG. 14 illustrates an example embodiment where the operation 1302 of the example operational flow 400 of FIG. 13 may include at least one additional operation. Additional operations may include an operation 1402, 1404, 1406 and/or 1408.

Operation 1402 illustrates sampling at least a portion of the communication content including at least one indicia of deception. For example, as shown in FIGS. 1 and 3B, during a communication interaction, the deceptive indicia detection module 115 may detect an incidence of indicia of deception. The deceptive indicia detection module 115 may sample a portion of the communications content 102 containing the detected incidence of indicia of deception and store an audio/video file containing the sampled portion of the communications content 102 containing the detected incidence of indicia of deception to a deceptive indicia library database 129. The audio/video file containing the sampled portion of the communications content 102 containing the detected incidence of indicia of deception may be annotated with information regarding the indicia of deception (e.g. the type of indicia of deception, the degree of deception indicated, etc.) to facilitate review of the detected indicia of deception.

Operation 1404 illustrates inserting a graphical element associated with associated with one or more indicia of deception into a video data file associated with the communication content. For example, as shown in FIGS. 1 and 3B, during a communication interaction, the deceptive indicia detection module 115 may detect an incidence of indicia of deception. The deceptive indicia detection module 115 may record the communications content 102 as an audio/video file and apply a graphical element (e.g. a "flag" icon 132) to the audio/video file at a time associated with the detection of an incidence of indicia of deception. The recorded audio/video file containing the graphical element communications content 102 associated with the detected incidence of indicia of deception may be stored to the deceptive indicia library database 129.

Operation 1406 illustrates storing one or more time stamps associated with one or more indicia of deception. For example, as shown in FIGS. 1 and 3B, during a communication interaction, the deceptive indicia detection module 115 may detect an incidence of indicia of deception. The deceptive indicia detection module 115 may store a time stamp associated with the detected incidence of the indicia of deception to the deceptive indicia library database 129.

Operation 1406 illustrates tagging the communication content according to one or more indicia of deception in response to a user input. For example, as shown in FIGS. 1 and 3B, a content-generating participant 103 may be independently aware of an occurrence of an indicia of deception contained in the communications content 102 (e.g. the content-generating participant 103 knows they have lied about a maximum authorized purchase price during a negotiation). In such a case, the communications content transmitting system 100 may receive a user input (e.g. a keystroke) via user input device 121 indicative of an occurrence of indicia of deception in the communications content 102. The deceptive indicia detection module 115 may correlate the occurrence of the user input to detected indicia of deception and apply a tag (e.g. an audio/video sample, an insertion of a graphical element, storing a time stamp, etc.) to the communications content 102 according to the user input.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

What is claimed is:

1. A system comprising:
   at least one computing device; and
   one or more instructions that, when implemented in the computing device, configure the at least one computing device for:
      receiving audio and/or video conferencing data representing a first participant in at least one conferencing interaction with at least one second participant;
      receiving audio and/or video conferencing data representing the at least one second participant in the at least one conferencing interaction with the first participant;
      detecting one or more physiological indicia of deception by the first participant in the audio and/or video conferencing data representing the first participant in the at least one conferencing interaction; and
      presenting, to the second participant via a conferencing user interface presenting the at least one conferencing interaction to the second participant, at least one indicator indicating a detection of one or more physiological indicia of deception by the first participant occurring during the at least one conferencing interaction.

2. The system of claim 1, wherein the detecting one or more physiological indicia of deception by the first participant in the audio and/or video conferencing data representing the first participant in the at least one conferencing interaction includes:
   detecting one or more micro expressions of the first participant in video data representing the first participant in at the least one conferencing interaction.

3. The system of claim 1, wherein the detecting one or more physiological indicia of deception by the first participant in the audio and/or video conferencing data representing the first participant in the at least one conferencing interaction includes:
   detecting an eye dilation of the first participant in video data representing the first participant in the least one conferencing interaction.

4. The system of claim 1, wherein the detecting one or more physiological indicia of deception by the first participant in the audio and/or video conferencing data representing the first participant in the at least one conferencing interaction includes:
   detecting an eye movement of the first participant in video data representing the first participant in the least one conferencing interaction.

5. The system of claim 1, wherein the detecting one or more physiological indicia of deception by the first participant in the audio and/or video conferencing data representing the first participant in the at least one conferencing interaction includes:
   detecting a heart rate of the first participant in audio and/or video data representing the first participant in the at least one conferencing interaction.

6. The system of claim 1, wherein the detecting one or more physiological indicia of deception by the first participant in the audio and/or video conferencing data representing the first participant in the at least one conferencing interaction includes:

detecting a blood pressure of the first participant in video data representing the first participant in the at least one conferencing interaction.

7. The system of claim 1, wherein the detecting one or more physiological indicia of deception by the first participant in the audio and/or video conferencing data representing the first participant in the at least one conferencing interaction includes:
   detecting a perspiration level of the first participant in video data representing the first participant in the at least one conferencing interaction.

8. The system of claim 1, wherein the detecting one or more physiological indicia of deception by the first participant in the audio and/or video conferencing data representing the first participant in the at least one conferencing interaction includes:
   detecting a breathing rate of the first participant in audio and/or video data representing the first participant in the at least one conferencing interaction.

9. The system of claim 1, wherein the detecting one or more physiological indicia of deception by the first participant in the audio and/or video conferencing data representing the first participant in the at least one conferencing interaction includes:
   detecting voice stress of the first participant in audio and/or video data representing the first participant in the at least one conferencing interaction.

10. The system of claim 1, wherein the detecting one or more physiological indicia of deception by the first participant in the audio and/or video conferencing data representing the first participant in the at least one conferencing interaction includes:
    detecting characteristic language in audio data representing the first participant in the at least one conferencing interaction.

11. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:
    displaying, to the second participant via a conferencing user interface presenting the at least one conferencing interaction to the second participant, at least one visual indicator indicative of a number of instances of physiological indicia of deception by the first participant detected during the at least one audio or audio/video conferencing interaction.

12. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:
    displaying, to the second participant via a conferencing user interface presenting the at least one conferencing interaction to the second participant, at least one visual indicator indicative of a rate of occurrences of physiological indicia of deception by the first participant detected during the at least one audio or audio/video conferencing interaction.

13. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:
    displaying, to the second participant via a conferencing user interface presenting the at least one conferencing interaction to the second participant, at least one color coded visual indicator indicative of one or more instances of physiological indicia of deception by the first participant detected during the at least one audio or audio/video conferencing interaction.

14. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:
    displaying, to the second participant within a specified half of a conferencing user interface presenting the conferencing interaction to the second participant, at least one visual indicator indicative of one or more physiological indicia of deception by the first participant detected during the at least one audio or audio/video conferencing interaction.

15. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:
    emitting, to the second participant via an audio or audio/video conferencing user interface presenting the audio or audio/video conferencing interaction to the second participant, an audible notification indicative of one or more physiological indicia of deception by the first participant detected during the at least one audio or audio/video conferencing interaction.

16. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:
    presenting, to the second participant via a conferencing user interface presenting the at least one conferencing interaction to the second participant, a predictive notification of one or more potential physiological indicia of deception by the first participant during the at least one conferencing interaction.

17. The system of claim 16, wherein the presenting, to the second participant via a conferencing user interface presenting the at least one conferencing interaction to the second participant, a predictive notification of one or more potential physiological indicia of deception by the first participant during the at least one conferencing interaction includes:
    providing, to the second participant via a conferencing user interface presenting the at least one audio or audio/video conferencing interaction to the second participant, a notification indicative of a comparison of the audio and/or video data representing the first participant in the at least one conferencing interaction to at least a first threshold value and a second threshold value.

18. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:

displaying the indicator during presentation of the at least one conferencing interaction.

19. The system of claim 1, wherein the presenting, to the second participant via a conferencing user interface presenting the at least one conferencing interaction to the second participant, at least one indicator indicating a detection of one or more physiological indicia of deception by the first participant occurring during the at least one conferencing interaction includes:

displaying the visual indicator during playback of the at least one conferencing interaction.

20. The system of claim 1, further comprising:
one or more instructions that, when implemented in the computing device, configure the
at least one computing device for:
tagging the audio and/or video conferencing data representing the first participant in the at least one conferencing interaction according to a detection of one or more physiological indicia of deception by the first participant.

21. The system of claim 20, wherein the tagging the audio and/or video conferencing data representing the first participant in the at least one conferencing interaction according to a detection of one or more physiological indicia of deception by the first participant includes:

sampling at least a portion of the audio and/or video conferencing data representing the first participant in the at least one conferencing interaction including at least one detected physiological indicia of deception by the first participant.

22. The system of claim 20 wherein the tagging the audio and/or video conferencing data representing the first participant in the at least one conferencing interaction according to a detection of one or more physiological indicia of deception by the first participant includes:

inserting a graphical element into a video data file representing the audio and/or video conferencing data representing the first participant in the at least one conferencing interaction.

23. The system of claim 20, wherein the tagging the audio and/or video conferencing data representing the first participant in the at least one conferencing interaction according to a detection of one or more physiological indicia of deception by the first participant includes:

storing one or more time stamps corresponding to a detection of one or more physiological indicia of deception by the first participant in the audio and/or video conferencing data representing the first participant in the at least one conferencing interaction.

24. The system of claim 20, wherein the tagging the audio and/or video conferencing data representing the first participant in the at least one conferencing interaction according to a detection of one or more physiological indicia of deception by the first participant includes:

tagging the audio and/or video conferencing data representing the first participant in the at least one conferencing interaction according to a detection of one or more physiological indicia of deception by the first participant in response to a user input.

25. A method comprising:
receiving audio and/or video conferencing data representing a first participant in at least one conferencing interaction with at least one second participant;
receiving audio and/or video conferencing data representing the at least one second participant in the at least one conferencing interaction with the first participant;
detecting one or more physiological indicia of deception by the first participant in the audio and/or video conferencing data representing the first participant in the at least one conferencing interaction; and
presenting, to the second participant via a conferencing user interface presenting the at least one conferencing interaction to the second participant, at least one indicator indicating a detection of one or more physiological indicia of deception by the first participant occurring during the at least one conferencing interaction.

26. A non-transitory computer-readable medium comprising computer-readable instructions for executing a computer implemented method, the method comprising:
receiving audio and/or video conferencing data representing a first participant in at least one conferencing interaction with at least one second participant;
receiving audio and/or video conferencing data representing the at least one second participant in the at least one conferencing interaction with the first participant;
detecting one or more physiological indicia of deception by the first participant in the audio and/or video conferencing data representing the first participant in the at least one conferencing interaction; and
presenting, to the second participant via a conferencing user interface presenting the at least one conferencing interaction to the second participant, at least one indicator indicating a detection of one or more physiological indicia of deception by the first participant occurring during the at least one conferencing interaction.

* * * * *